(12) United States Patent
Chazal et al.

(10) Patent No.: US 10,126,154 B2
(45) Date of Patent: Nov. 13, 2018

(54) SPECTRAL ANALYSIS WITH SPECTRUM DECONVOLUTION

(71) Applicant: SCHLUMBERGER TECHNOLOGY CORPORATION, Sugar Land, TX (US)

(72) Inventors: Damien Chazal, Singapore (SG); Massimiliano Fiore, Singapore (SG)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/034,824

(22) PCT Filed: Nov. 7, 2014

(86) PCT No.: PCT/US2014/064532
§ 371 (c)(1),
(2) Date: May 5, 2016

(87) PCT Pub. No.: WO2015/070008
PCT Pub. Date: May 14, 2015

(65) Prior Publication Data
US 2016/0290846 A1  Oct. 6, 2016

(30) Foreign Application Priority Data

Nov. 8, 2013 (EP) ..................................... 13306528
Nov. 8, 2013 (EP) ..................................... 13306529

(51) Int. Cl.
*G01F 1/66* (2006.01)
*G01N 23/12* (2006.01)
(Continued)

(52) U.S. Cl.
CPC ................ *G01F 1/66* (2013.01); *E21B 47/10* (2013.01); *G01N 23/12* (2013.01); *G01N 33/2823* (2013.01); *G01T 1/20* (2013.01)

(58) Field of Classification Search
CPC ...... G01N 23/12; G01N 33/2823; G01T 1/20; G01F 1/66; E21B 47/10
(Continued)

(56) References Cited

U.S. PATENT DOCUMENTS 4,688,198 A * 8/1987 Wiggins ................. G01V 1/364
367/46
4,841,490 A * 6/1989 Carron ..................... G01V 1/28
367/38
(Continued)

FOREIGN PATENT DOCUMENTS

CN        1469720 A     1/2004
CN      101061504 A    10/2007
(Continued)

OTHER PUBLICATIONS

Extended European Search Report issued in related EP Application No. 13306528.4 dated Feb. 6, 2014 (8 pages).
(Continued)

*Primary Examiner* — David Porta
*Assistant Examiner* — Blake Riddick
(74) *Attorney, Agent, or Firm* — Cameron R. Sneddon; Lee Eubanks

(57) ABSTRACT

A method for inferring incident count rates of electromagnetic energy at a detector is provided. In one embodiment, the method includes transmitting electromagnetic radiation through a fluid and receiving a portion of the electromagnetic radiation at a detector. The method also includes measuring the energy spectrum of the portion of the electromagnetic radiation received by the detector and using the
(Continued)

measured energy spectrum and a physical model of detector response to electromagnetic radiation to infer incident count rates for discrete energy levels of the portion of the electromagnetic radiation received by the detector. Additional systems, devices, and methods are also disclosed.

19 Claims, 12 Drawing Sheets

(51) Int. Cl.
G01N 33/28 (2006.01)
E21B 47/10 (2012.01)
G01T 1/20 (2006.01)

(58) Field of Classification Search
USPC ... 250/256, 261, 269.1, 269.3, 252.1, 361 R, 250/356.1
See application file for complete search history.

(56) References Cited

U.S. PATENT DOCUMENTS

| | | | | |
|---|---|---|---|---|
| 4,857,729 | A * | 8/1989 | Gadeken | E21B 47/1015 250/256 |
| 5,148,405 | A | 9/1992 | Belchamber et al. | |
| 5,161,409 | A * | 11/1992 | Hughes | E21B 21/08 250/255 |
| 5,350,925 | A * | 9/1994 | Watson | G01V 5/12 250/264 |
| 5,360,738 | A * | 11/1994 | Jones | E21B 21/08 250/255 |
| 5,475,220 | A * | 12/1995 | Hughes | G01N 33/383 250/339.08 |
| 5,557,103 | A * | 9/1996 | Hughes | G01N 33/2823 250/255 |
| 5,608,215 | A * | 3/1997 | Evans | G01V 5/101 250/254 |
| 5,804,820 | A * | 9/1998 | Evans | G01V 5/101 250/269.2 |
| 5,850,623 | A * | 12/1998 | Carman, Jr. | G01J 3/28 250/252.1 |
| 6,097,766 | A | 8/2000 | Groves et al. | |
| 6,405,604 | B1 | 6/2002 | Berard et al. | |
| 6,686,589 | B2 * | 2/2004 | Fitzgerald | G01V 5/04 250/256 |
| 6,958,604 | B2 * | 10/2005 | An | G01V 3/32 324/300 |
| 7,462,837 | B2 * | 12/2008 | Russ | G01T 1/36 250/252.1 |
| 7,617,055 | B2 | 11/2009 | Henry et al. | |
| 7,661,302 | B2 | 2/2010 | Gysling | |
| 7,908,930 | B2 | 3/2011 | Xie et al. | |
| 8,259,299 | B2 | 9/2012 | Harra et al. | |
| 8,290,721 | B2 | 10/2012 | Wehrs et al. | |
| 8,565,860 | B2 | 10/2013 | Kimchy et al. | |
| 9,217,802 | B2 * | 12/2015 | Muhl | G01V 1/325 |
| 2005/0122840 | A1 * | 6/2005 | Haldorsen | G01V 1/37 367/57 |
| 2005/0273266 | A1 * | 12/2005 | Nickel | G01V 1/286 702/14 |
| 2006/0065824 | A1 * | 3/2006 | Mickael | E21B 47/0005 250/252.1 |
| 2006/0180767 | A1 * | 8/2006 | Ramsden | G01T 1/1642 250/369 |
| 2007/0006640 | A1 | 1/2007 | Gysling | |
| 2007/0064532 | A1 * | 3/2007 | Haldorsen | G01V 1/37 367/57 |
| 2007/0284518 | A1 * | 12/2007 | Randall | G01T 7/005 250/261 |
| 2009/0213691 | A1 * | 8/2009 | Christie | G01V 1/364 367/43 |
| 2009/0241672 | A1 | 10/2009 | Gysling | |
| 2010/0139417 | A1 | 6/2010 | Kolahi | |
| 2010/0305873 | A1 | 12/2010 | Sjoden et al. | |
| 2014/0208826 | A1 * | 7/2014 | Larter | E21B 49/06 73/23.41 |
| 2014/0355737 | A1 * | 12/2014 | Korkin | G01N 23/12 378/53 |
| 2015/0219782 | A1 * | 8/2015 | Kadayam Viswanathan | G01V 3/32 324/309 |
| 2016/0290841 | A1 | 10/2016 | Cadalen et al. | |

FOREIGN PATENT DOCUMENTS

| | | |
|---|---|---|
| CN | 101946173 A | 1/2011 |
| EP | 1970702 A1 | 9/2008 |
| EP | 2574919 A1 | 4/2013 |
| EP | 2871478 A1 | 5/2015 |
| FR | 2818379 A1 | 6/2002 |
| GB | 2439423 A | 12/2007 |
| RU | 2164367 C2 | 6/2002 |
| RU | 2466383 C2 | 11/2012 |
| WO | WO9614559 A1 | 5/1996 |
| WO | 0125762 A1 | 4/2001 |
| WO | 0250522 A1 | 6/2002 |
| WO | WO2008107181 A1 | 9/2008 |
| WO | 2009036337 A2 | 3/2009 |
| WO | 2009058964 A1 | 5/2009 |
| WO | 2010066994 A1 | 6/2010 |
| WO | 2012158759 A2 | 11/2012 |

OTHER PUBLICATIONS

Extended European Search Report issued in related EP Application No. 13306529.2 dated Apr. 2, 2014 (8 pages).
International Search Report and Written Opinion issued in related International Application No. PCT/US2014/064532 dated Feb. 23, 2015 (12 pages).
Krumrey et al., "Calibration and characterization of semiconductor X-ray detectors with synchrotron radiation", Nuclear Instruments and Methods in Physics Research A, vol. 568, No. 1, Nov. 2006, pp. 364-368.
LaVigne et al., "Extraordinary improvement in scintillation detectors via post-processing with ASEDRA-solution to a 50-year-old problem", SPIE Proceedings vol. 6954, 2008, 11 pages.
LeClair et al., "An analytic model for the response of a CZT detector in diagnostic energy dispersive x-ray spectroscopy", Medical Physics, vol. 33, No. 5, May 2006, pp. 1329-1337.
Meng et al., "An Inter-comparison of Three Spectral-Deconvolution Algorithms for Gamma-ray Spectroscopy", IEEE Transactions on Nuclear Science, vol. 47, No. 4, Aug. 2000, pp. 1329-1336.
Sood et al., "A new Monte Carlo assisted approach to detector response functions", Nuclear Instruments and Methods in Physics Research B, vol. 213, 2004, pp. 100-104.
Wielopolski et al., "Prediction of the Pulse-Height Spectral Distortion Caused by the Peak Pile-Up Effect", Nuclear Instruments and Methods, vol. 133, 1976, pp. 303-309.
Office Action received in the related CN Application 201480071435.3 dated Mar. 1, 2018 (11 pages).
Examination Report issued in the related SA application 516371084 dated Jun. 3, 2018.
Office Action issued in the related EP application 13306529.2, dated May 4, 2018 (8 pages).
International Preliminary Report on Patentability issued in the related PCT Application PCT/US2014/064532, dated May 10, 2016 (10 pages).
Office Action issued in the related EP application 13306529.2, dated Sep. 1, 2017 (6 pages).
Office Action issued in the related RU application 2016122471, dated May 11, 2017 (17 pages).
International Search Report and Written Opinion issued in the related PCT application PCT/US14/6451, dated Feb. 9, 2015 (8 pages).

(56) References Cited

OTHER PUBLICATIONS

International Preliminary Report on Patentability issued in the related PCT application PCT/US14/64514, dated May 10, 2016 (6 pages).
Office action issued in the related RU application 2016120730, dated Mar. 29, 2017 (14 pages).
European Search Report issued in the related EP Application 14861011.6, dated May 17, 2017 (3 pages).
Communication Article 94-3 issued in the related EP Application 14861011.6, dated Jun. 1, 2017 (5 pages).
Decision of Grant issued in the related RU Application 201612070, dated May 25, 2017 (21 pages).
Decision of Grant issued in the related RU Application 2016122471, dated Jun. 28, 2018 (19 pages).

\* cited by examiner

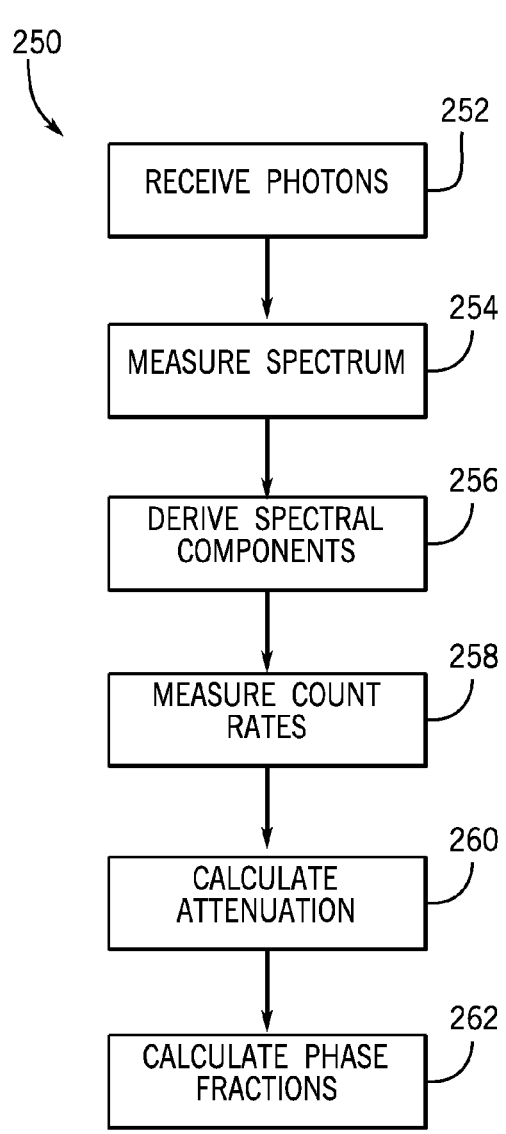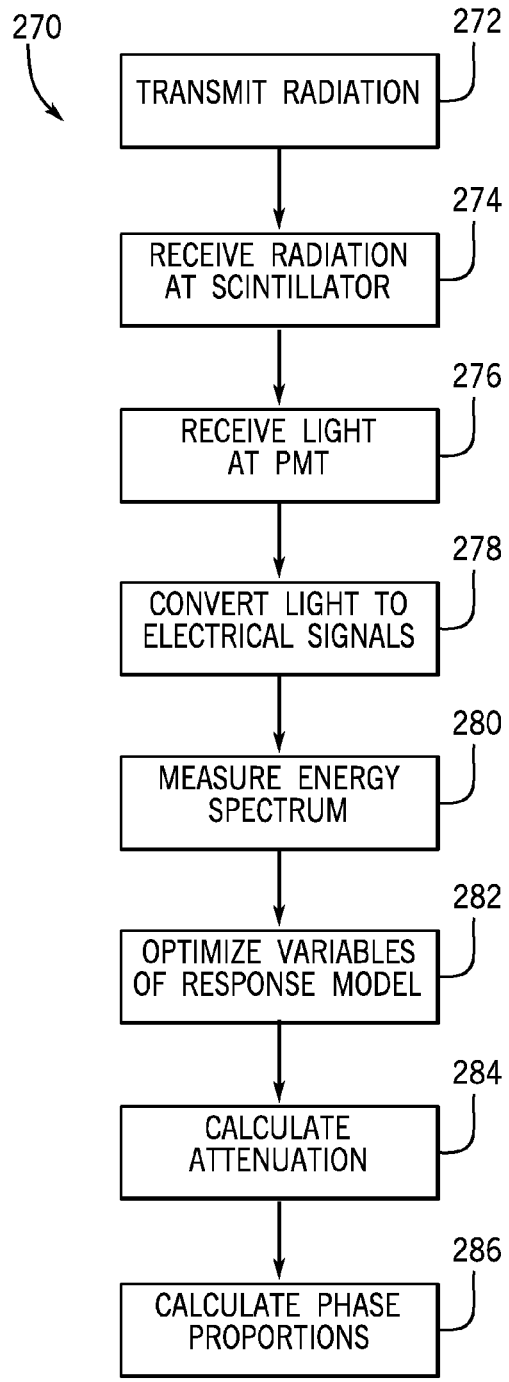
FIG. 28
FIG. 29

SPECTRAL ANALYSIS WITH SPECTRUM DECONVOLUTION

BACKGROUND

The present disclosure relates to methods and devices for determining the flow rate and/or phase fraction of various components in a multiphase fluid flow, sometimes referred to as multiphase flow meters (MPFM).

DESCRIPTION OF THE RELATED ART

Wells are generally drilled into subsurface rocks to access fluids, such as hydrocarbons, stored in subterranean formations. The subterranean fluids can be produced from these wells through known techniques. Operators may want to know certain characteristics of produced fluids to facilitate efficient and economic exploration and production. For example, operators may want to know flow rates of produced fluids. These produced fluids are often multiphase fluids (e.g., those having some combination of water, oil, and gas), making measurement of the flow rates more complex.

Various systems can be used to determine flow rates for multiphase fluids. In some systems, multiphase fluids are separated into their constituent phases and these phases are then individually tested to determine flow rates. Other systems include multiphase flow meters that can be used to measure flow rates of multiphase fluids without separation. These multiphase flow meters may be smaller and lighter than traditional separators and test units, and the ability to measure flow rates without separation may be desirable in some instances. Both the traditional separator systems and the multiphase flow meter systems can also be used to determine certain other fluid characteristics of interest.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present disclosure, a method includes transmitting electromagnetic radiation through a fluid and receiving a portion of the electromagnetic radiation at a detector. The method also includes measuring the energy spectrum of the portion of the electromagnetic radiation received by the detector and using the measured energy spectrum and a physical model of detector response to electromagnetic radiation to infer incident count rates for discrete energy levels of the portion of the electromagnetic radiation received by the detector.

In another embodiment, a method of determining phase fractions for a multiphase fluid includes receiving electromagnetic radiation transmitted through the multiphase fluid and incident on an electromagnetic radiation detector, as well as transforming the incident electromagnetic radiation to electrical signals representative of the incident electromagnetic radiation. The method also includes determining an energy spectrum from the electrical signals and deconvolving the determined energy spectrum to estimate quantities of photons for different energy levels in the electromagnetic radiation that are received by the electromagnetic radiation detector. Additionally, the method includes calculating attenuation coefficients for phases of the multiphase fluid for the different energy levels based on the estimated quantities of photons of the different energy levels received by the electromagnetic radiation detector, and determining the phase fractions for the phases of the multiphase fluid based on the calculated attenuation coefficients.

In another embodiment of the present disclosure, an apparatus includes a fluid conduit; a radioactive source coupled to the fluid conduit; and a sensor coupled to the fluid conduit to receive electromagnetic radiation from the radioactive source, measure the energy spectrum of the received electromagnetic radiation, and output data indicative of the measured energy spectrum. The apparatus also includes a controller to receive the output data from the sensor and to determine, through deconvolution of the measured energy spectrum, count rates for photons of different energy levels in the electromagnetic radiation received by the sensor.

In still another embodiment, a method includes receiving photons having different energies at a detector and measuring an energy spectrum of the photons. Additionally, the method includes using multiple monoenergetic response functions to derive spectral components of the energy spectrum for multiple energy levels of the photons and measuring count rates for energy levels of the received photons based on the derived spectral components.

In yet another embodiment of the present disclosure, an apparatus includes a detector of electromagnetic radiation and a multi-channel analyzer to measure an energy spectrum of electromagnetic radiation received by the detector. Further, the apparatus includes a controller to deconvolve the measured energy spectrum using a physical model representative of the response of the detector to characterize the electromagnetic radiation received by the detector.

In an additional embodiment, a method includes modeling a response function of a detector assembly to electromagnetic radiation, the detector assembly having a scintillation crystal, a photomultiplier tube, and an amplifier. Modeling this response function of the detector includes determining a crystal response function that relates an electromagnetic spectrum incident on the scintillation crystal of the detector assembly to an electromagnetic spectrum deposited in the scintillation crystal. Modeling the response function of the detector also includes determining a photomultiplier tube response function that relates the electromagnetic spectrum deposited in the scintillation crystal to a smeared spectrum and determining an amplifier response function that relates the smeared spectrum to an observed spectrum. The response function can be defined as the convolution product of the electromagnetic spectrum incident on the scintillation crystal, the crystal response function, the photomultiplier tube response function, and the amplifier response function.

In one embodiment, a method includes transmitting electromagnetic radiation from a source through a fluid in a conduit and receiving an attenuated portion of the electromagnetic radiation at a scintillation crystal of a detector. The method also includes receiving, at a photomultiplier tube of the detector, light emitted from the scintillation crystal in response to receipt of the attenuated portion of the electromagnetic radiation received at the scintillation crystal; converting the light received at the photomultiplier tube into electrical signals; and measuring, based on the electrical signals, an energy spectrum generated by the attenuated portion of the electromagnetic radiation. Additionally, the method includes optimizing variables of a response model for the detector to minimize residuals between the measured energy spectrum and an output of the response model. The optimized variables can include incident count rates for different energy levels of photons received by the scintillation crystal and detector-specific parameters.

In a further embodiment, a multiphase flow meter includes a fluid conduit, as well as an emitter and a detector of electromagnetic radiation arranged with respect to the fluid conduit so as to enable the detector to receive photons transmitted from the emitter through a fluid within the fluid conduit. The detector can include a scintillator, a photomultiplier tube, and an amplifier. The multiphase flow meter also includes a multi-channel analyzer coupled to the detector to receive electrical signals from the amplifier and output a measured energy spectrum of the photons received by the detector and a flow computer encoded with a response model for the detector. The response model can be based on characteristics of the emitter and the detector, and the flow computer can compare the measured energy spectrum with the response model to infer count rates for the photons received by the detector.

Additionally, in one embodiment a device includes a non-transitory, computer-readable storage medium encoded with application instructions. When executed by a processor, the application instructions enable receiving a measured spectrum representative of electromagnetic radiation incident on a detector, fitting a modeled spectrum to the measured spectrum, and determining from the modeled spectrum count rates for photons of the electromagnetic radiation incident on the detector.

Various refinements of the features noted above may exist in relation to various aspects of the present embodiments. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein:

FIG. 28 is a flow chart for calculating incident count rates, attenuation, and phase fractions of a fluid in accordance with one embodiment; and FIG. 29 is a flow chart for optimizing variables of a detector response model to calculate characteristics of a fluid of interest in accordance with one embodiment.

DETAILED DESCRIPTION

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

Figure 1:
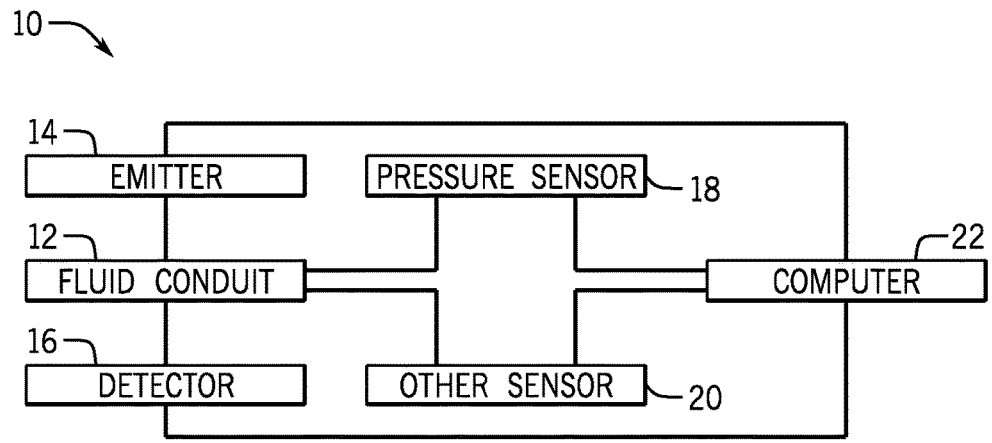
FIG. 1 generally depicts an apparatus in the form of a flow meter for analyzing a fluid in accordance with one embodiment of the present disclosure.

Turning now to the drawings, an apparatus 10 in the form of a flow meter is generally depicted in FIG. 1 in accordance with one embodiment. While certain elements of the apparatus 10 are depicted in this figure and generally discussed below, it will be appreciated that the apparatus 10 may include other components in addition to, or in place of, those presently illustrated and discussed. Moreover, while the apparatus 10 may be provided in the form of a flow meter (e.g., a multiphase flow meter) as described below in connection with certain embodiments, the apparatus 10 could be provided in other forms as well.

As depicted, the apparatus includes a fluid conduit 12 for receiving a fluid. The apparatus 10 also includes an emitter 14 of electromagnetic radiation, a detector 16 of electromagnetic radiation, a pressure sensor 18 (e.g., one or both of a pressure transmitter and a differential-pressure transmitter), and one or more additional sensors 20 (e.g., a temperature sensor). To facilitate certain measurements, such as flow rate, the fluid conduit 12 can have a tapered bore (e.g., a Venturi throat) to constrict fluid flow. Further, in at least one embodiment the emitter 14 and detector 16 are positioned about a Venturi throat in the fluid conduit 12 such that the detector 16 receives radiation that has been transmitted through fluid within the Venturi throat.

The apparatus 10 further includes a computer 22 (which may also be variously referred to as a controller or a control unit) for determining characteristics of fluid within the fluid conduit 12. In at least some embodiments, the computer 22 is provided in the form of a flow computer coupled with the other depicted components in a single unit to facilitate installation of a flow meter in a larger system (e.g., an oilfield apparatus). More specifically, the computer 22 is operable to determine characteristics of fluid within the fluid conduit 12 from measurements collected by the other components. For example, the computer 22 can determine pressure and flow rate of the fluid. Further, a computer 22 of a multiphase flow meter can determine the attenuation of the fluid with respect to various levels of electromagnetic radiation by comparing the amount of radiation emitted from the emitter 14 to the portion of such radiation actually received by the detector 16. Such a computer 22 can also use this information to calculate phase fractions (e.g., proportions of oil, gas, and water) for a multiphase fluid within the fluid conduit 12. Finally, single-phase flow rates can be achieved by combining the phase fraction measurements together with the total flow rate measurement. Often, a multiphase flow model is implemented to compensate for differences between the velocities of liquid and gas in the fluid.

Figure 2:
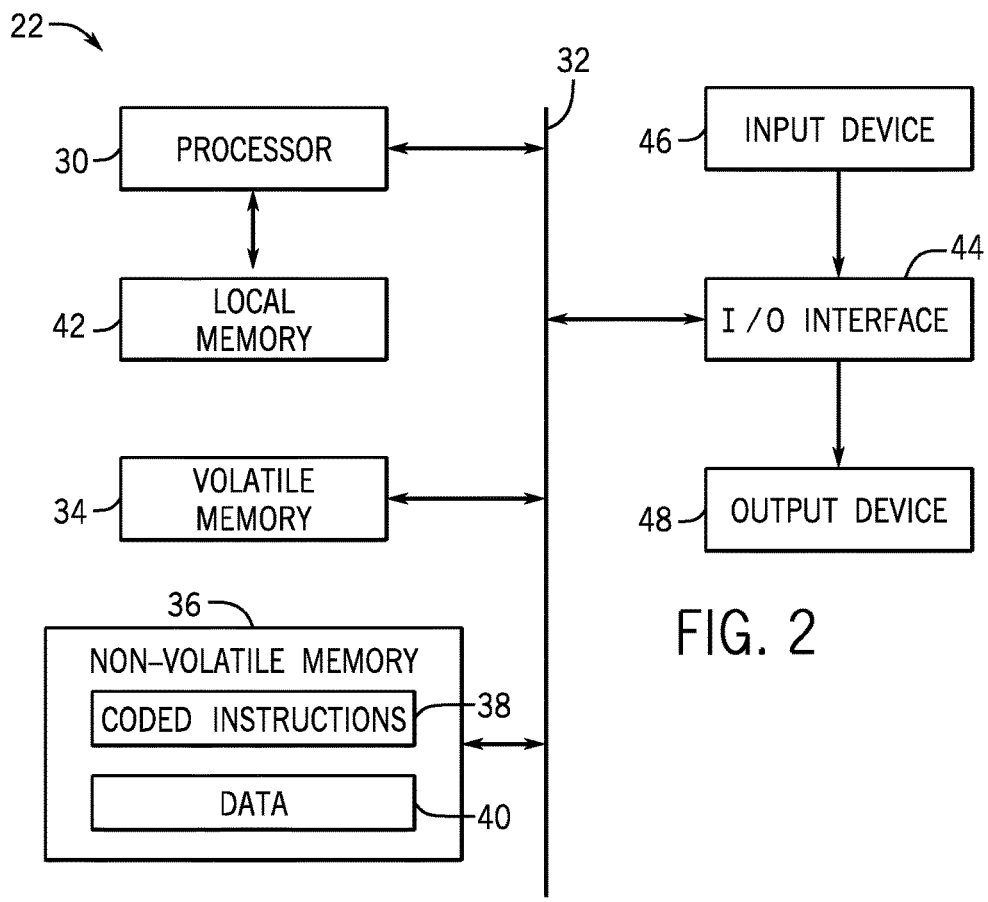
FIG. 2 is a block diagram of components of a computer of the apparatus of FIG. 1 in accordance with one embodiment.

The computer 22 can be a processor-based system, an example of which is provided in FIG. 2. In this depicted embodiment, the computer 22 includes at least one processor 30 connected, by a bus 32, to volatile memory 34 (e.g., random-access memory) and non-volatile memory 36 (e.g., flash memory and a read-only memory (ROM)). Coded application instructions 38 and data 40 are stored in the non-volatile memory 34. For example, the application instructions 38 can be stored in a ROM and the data 40 can be stored in a flash memory. The instructions 38 and the data 40 may be also be loaded into the volatile memory 34 (or in a local memory 42 of the processor) as desired, such as to reduce latency and increase operating efficiency of the computer 22. The coded application instructions 38 can be provided as software that may be executed by the processor 30 to enable various functionalities described herein. Non-limiting examples of these functionalities include deconvolution of a measured energy spectrum, determination of incident photon count rates on a detector, and calculation of attenuation rates and phase fractions for a fluid. In at least some embodiments, the application instructions 38 are encoded in a non-transitory computer readable storage medium, such as the volatile memory 34, the non-volatile memory 36, the local memory 42, or a portable storage device (e.g., a flash drive or a compact disc).

An interface 44 of the computer 22 enables communication between the processor 30 and various input devices 46 and output devices 48. The interface 44 can include any suitable device that enables such communication, such as a modem or a serial port. In some embodiments, the input devices 46 include one or more sensing components of the apparatus 10 (e.g., detector 16, pressure sensors 18, other sensors 20) and the output devices 48 include displays, printers, and storage devices that allow output of data received or generated by the computer 22. Input devices 46 and output devices 48 may be provided as part of the computer 22 or may be separately provided.

Further, while the computer 22 could be located with the fluid conduit 12 and sensing components of the apparatus 10 as a unitary system (e.g., a flow meter), the computer 22 could also be located remote from the other components. Further, the computer 22 could be provided as a distributed system with a portion of the computer 22 located with the sensing components at the fluid conduit 12 and the remaining portion of the computer 22 located remote from the fluid conduit 12.

Figure 3:
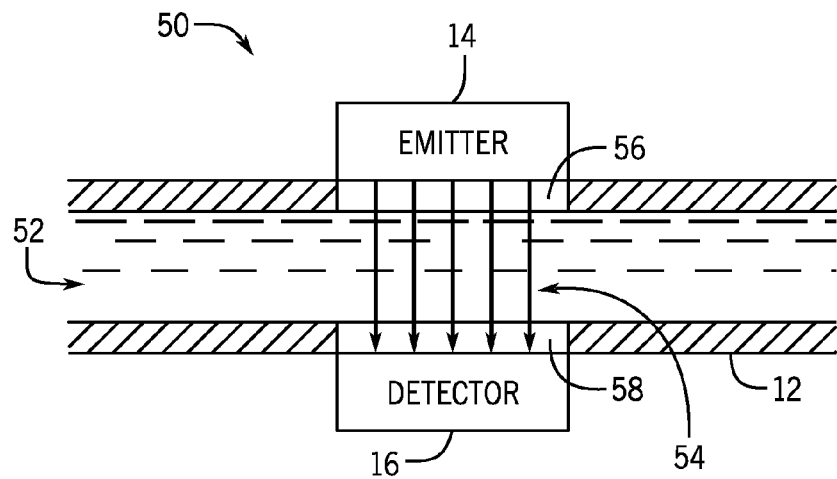
FIGS. 3 and 4 generally depict an emitter and a detector of electromagnetic radiation positioned about a fluid conduit to enable irradiation of fluid within the conduit and measurement of radiation transmitted through the fluid in accordance with one embodiment.
Figure 4:
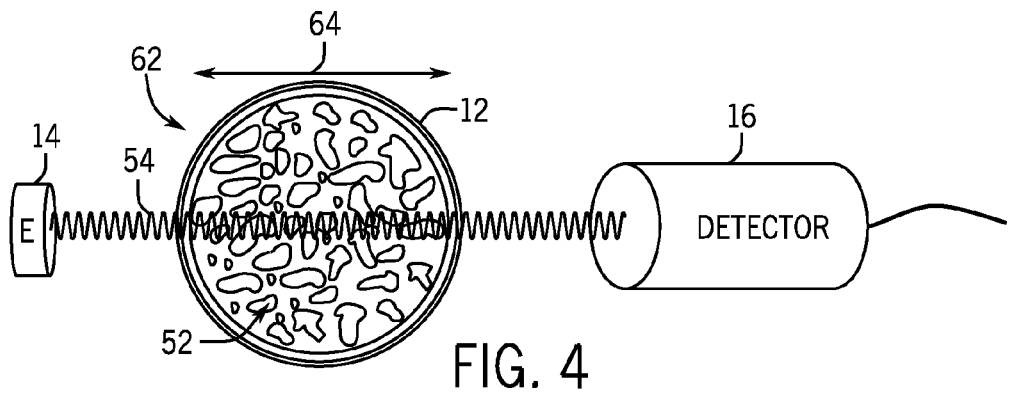

Additional details regarding operation of the emitter 14 and the detector 16 may be better understood with reference to FIGS. 3 and 4. The emitter 14 and the detector 16, which may also be referred to as components of a spectrometer or densitometer 50, are arranged about the fluid conduit 12 in any suitable manner that allows the detector 16 to receive electromagnetic radiation transmitted through fluid within the fluid conduit 12 from the emitter 14. As presently shown, the emitter 14 and the detector 16 are coupled opposite one another about the fluid conduit 12. Fluid 52 within the fluid conduit 12 is irradiated with electromagnetic radiation 54. Some of the electromagnetic radiation 54 is absorbed or scattered by the fluid 52, but a portion of the electromagnetic radiation 54 is received by the detector 16. Windows 56 and 58 isolate the emitter 14 and the detector 16 from the fluid 52, while still permitting the electromagnetic radiation 54 to be transmitted from the emitter 14 and received by the detector 16. Particularly, the windows 56 and 58 are at least partially transparent to electromagnetic radiation to be emitted from the emitter 14 and read by the detector 16.

The emitter 14 can produce electromagnetic radiation of any suitable frequency and energy within the electromagnetic spectrum. For instance, in some embodiments the emitter 14 includes one or more radioactive sources that emit gamma rays and x rays. Other embodiments could include non-radioactive emitters 14, such as an electric x-ray generator, in full accordance with the present techniques.

As generally shown in FIG. 4, the emitter 14 and the detector 16 can be positioned on opposite sides of a Venturi throat 62 in the fluid conduit 12. This arrangement allows measurement of the linear attenuation coefficient, $\lambda_m(E)$, of the fluid 52 for electromagnetic radiation at a given energy E according to the Beer-Lambert law:

$$\lambda_m(E) = \frac{1}{d} \ln(N_0(E)/N(E)),$$

in which d is the throat diameter 64, N(E) is the amount of transmitted photons (the quantity of photons detected by the detector 16), and $N_0(E)$ is the empty pipe count rates (the quantity of photons emitted from the emitter 14 that would reach the detector 16 but for interference by a medium, such as the fluid 52, in the throat 62).

In some instances, the analyzed fluid can have multiple phases. For example, the fluid 52 can be a multiphase fluid having an oily liquid phase, an aqueous liquid phase, and a gaseous phase, which may be more generally referred to as oil, water, and gas phases. It will be appreciated by those skilled in the art that the attenuation of electromagnetic radiation by a multiphase fluid is a linear combination of the attenuations caused by each of its phases weighted by their proportions in the fluid. In the case of a fluid having some combination of oil, water, and gas, this can be written as:

$$\lambda_m(E) = \lambda_g(E)\alpha_g + \lambda_w(E)\alpha_w + \lambda_o(E)\alpha_o,$$

where $\lambda g$, $\lambda w$, and $\lambda o$ are attenuation coefficients for gas, water, and oil for radiation of a given energy level E, and $\alpha g$, $\alpha w$, and $\alpha o$ are respective fractional portions of each phase within the analyzed fluid (also referred to herein as phase hold-ups or phase fractions).

This gives as many equations as the number of distinct energy levels in the electromagnetic radiation from the emitter 14. Further considering that the three phase hold-ups sum up to 1, the following system of linear equations can be achieved:

$$\begin{pmatrix} \lambda_g(E) & \lambda_w(E_1) & \lambda_o(E_1) \\ \vdots & \vdots & \vdots \\ \lambda_g(E_n) & \lambda_w(E_n) & \lambda_o(E_n) \\ 1 & 1 & 1 \end{pmatrix} \cdot \begin{pmatrix} \alpha_g \\ \alpha_w \\ \alpha_o \end{pmatrix} = \begin{pmatrix} \lambda_m(E_1) \\ \vdots \\ \lambda_m(E_n) \\ 1 \end{pmatrix}$$

The attenuation matrix above (i.e., the matrix including the phase-specific attenuation coefficients for n energy levels) can be obtained from full bore measurements on each phase, hereafter called the in-situ references, or theoretical coefficients can be used. This attenuation matrix can then be inverted (giving an inversion matrix $A^{-1}$) to calculate the phase hold-ups:

$$\begin{pmatrix} \alpha_g \\ \alpha_w \\ \alpha_o \end{pmatrix} = A^{-1} \cdot \begin{pmatrix} \lambda_m(E_1) \\ \vdots \\ \lambda_m(E_n) \\ 1 \end{pmatrix}$$

The equations above relating the phase attenuations and phase fractions to the measured attenuation coefficients for the multiphase fluid assume the energy levels $E_1 \ldots E_n$ emitted from a source can be independently measured by the detector. In reality, however, the detector response is not ideal and some higher-energy photons can be accounted in lower-energy regions or, conversely, lower-energy photons can be accounted in higher-energy regions. Due to this mixing of incident energies, the phase hold-ups can eventually be biased when inverting the attenuation matrix. Likewise, the detector response may drift over time because of temperature fluctuations or due to its own aging. As a consequence, the real-time count rates may differ from the in-situ references (which could have been acquired several days or months before, for example). This can also lead to a systematic error on the phase hold-ups.

To compensate for these two sources of error, each part of the detection process can be modeled. Moreover, rather than recording just certain electromagnetic emissions and then using an empirical model to compensate for variance between real and ideal detector response, at least some embodiments of the present disclosure use the detector 16 to measure the full energy spectrum of the electromagnetic radiation 54. And as described in greater detail below, such embodiments can then use a physical model of the response of the detector 16 to determine count rates for photons of different energy levels of interest that are incident on the detector 16. In at least some instances, the measurement of the full energy spectrum and use of the physical model enables the detection chain of the apparatus 10 to be insensitive to temperature, aging drifts, and source activity variations. These features also allow the presently disclosed techniques for determining incident count rates to be broadly applicable to any types of sources, detector technologies, and source-detector geometries.

Figure 5:
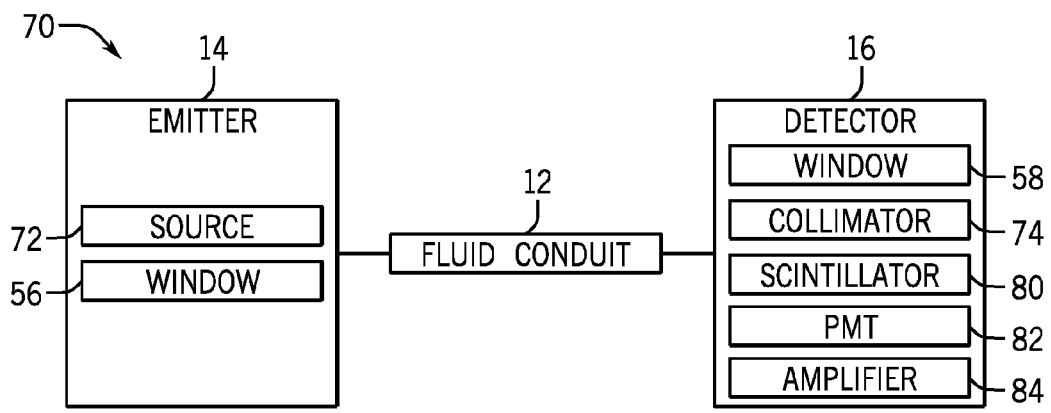
FIG. 5 is a block diagram of components of the emitter and detector of FIGS. 3 and 4 in accordance with one embodiment.

Additional features of the emitter 14 and the detector 16 are depicted in FIG. 5 as part of a system 70 in accordance with certain embodiments. In this example, the emitter 14 includes a source 72 of electromagnetic radiation. As noted above, the source 72 can be a radioactive source, such as barium-133 or americium 241. The selection of the source 72 can be based on the fluid intended to be analyzed. For instance, americium-241 could be used if the fluid 52 is a wet gas and barium-133 could be used in other cases. Fluorescent sources, which generally emit lower-energy spectra than radioactive sources, could also be used. In addition to the windows 56 and 58 described above, the system 70 includes a collimator 74. The collimator 74 has an opening, such as a slit, that forms a beam of electromagnetic radiation that is directed toward the scintillator 80. As presently depicted, the collimator 74 is on the detector side of the system, so that electromagnetic radiation transmitted through the fluid is collimated for receipt by the scintillator 80. This helps filter out scattered photons from the radiation passed to the scintillator 80. But the collimator 74 could be provided at other positions within the system 70.

The detector 16 is illustrated as a scintillation detector in FIG. 5, though the detector could be a solid-state detector in other embodiments. As depicted, the detector 16 includes a scintillator 80, a photomultiplier tube (PMT) 82, and an amplifier 84. The scintillator 80 can be provided in various forms, such as a crystal. In some embodiments, the scintillator 80 is an inorganic scintillation crystal.

Figure 6:
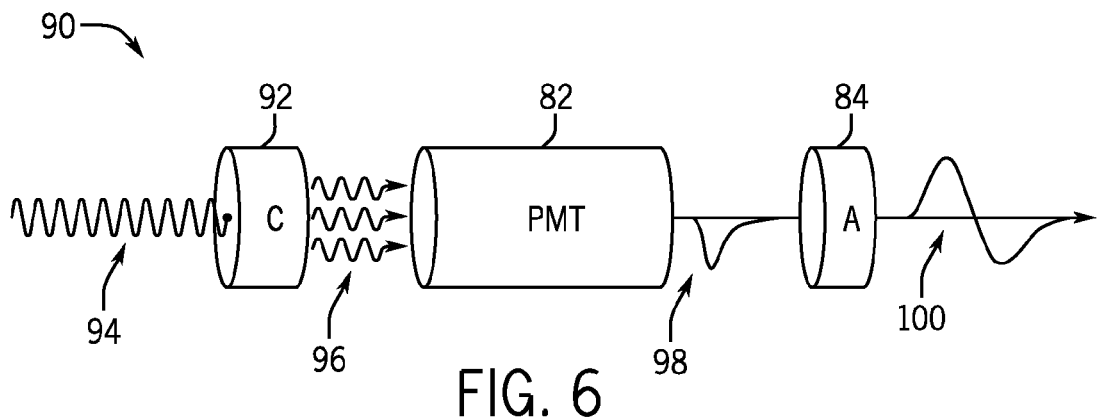
FIG. 6 generally depicts a detector having a scintillation crystal, a photomultiplier tube, and an amplifier in accordance with one embodiment.

The scintillator 80 collects at least a portion of the incident photon energy it receives and converts this incident energy into radiation in a different part of the electromagnetic spectrum. For example, as depicted as part of a detection chain 90 in FIG. 6, high-energy radiation 94 (e.g., x-rays and gamma rays) can be absorbed by the scintillator (here provided as a scintillation crystal 92) to cause it to radiate pulses of light 96, such as visible light. The PMT 82, which can be optically coupled to the scintillation crystal 92, detects electromagnetic radiation (e.g., light 96) emitted from the scintillation crystal 92 and converts this radiation into electrical charges 98. The amplifier 84 then transforms these electrical charges into electrical signals, such as voltage pulses 100, suitable for analog-to-digital processing.

In at least some embodiments, a physical model of the response of the detector 16 is created. The physical model can generally include models for each part of a detection chain. This physical model can also be stored in the computer 22 and, as described below, can be used to facilitate determination of incident count rates at the detector 16 and the calculation of phase fractions for an analyzed fluid.

Figure 7:
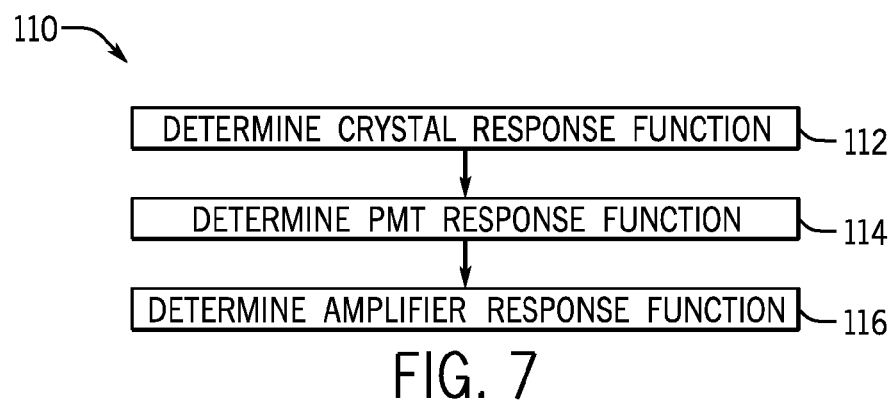
FIG. 7 is a flow chart for developing a response model for the detector of FIG. 6 in accordance with one embodiment.

One example of a process for creating a physical model of the response of a scintillation detector is generally represented by flow chart 110 in FIG. 7. In this embodiment, the components of the detection chain 90 are themselves modeled as response functions that relate inputs at each component to corresponding outputs. Particularly, as shown in FIG. 7, a response function for the scintillation crystal 92 is determined at block 112, a response function for the PMT 82 is determined at block 114, and a response function for the amplifier 84 is determined at block 116. It will be appreciated, however, that components of a solid-state detector could be similarly modeled in another embodiment. The determination of these response functions for a scintillation detector is described in greater detail below by way of example.

In x-ray and gamma-ray spectroscopy, photons deposit their energy into a detector (e.g., the scintillation crystal 92 or a semiconductor) through matter interaction effects, thus generating an energy spectrum. Even by considering an ideally perfect deposited-energy-to-electric-signal conversion process resulting in a discrete spectrum, due to the finite size of the detector the recovered spectrum is continuous: photons emitted with energy hv have a probability of being measured with smaller energies. As described in detail below, some embodiments of the present disclosure include inferring the number and energy of photons incident on the detector from a measured spectrum. It should be appreciated that the accuracy of such inferences in at least some embodiments will depend on the accuracy of a physical model of the detector response.

Determining the crystal response function at block 112 includes determining a crystal impulse response h(e', e) that relates an incident spectrum i(e) of the electromagnetic radiation 94 on the scintillation crystal 92 to a deposited spectrum d(e) inside the scintillation crystal. As will be appreciated, photons in the electromagnetic radiation 94 interact with atoms of the scintillation crystal 92 to generate light 96. Examples of such interactions are generally described below with reference to FIGS. 8-13. For the sake of simplicity, these examples depict photons with energy hv hitting a scintillation crystal 92 of finite size. Notable mechanisms of gamma-ray and x-ray interaction with matter include photoelectric absorption, Compton scattering (incoherent scattering), and, in the case of gamma-rays with energy hv>1.022 MeV, pair production.

Figure 8:
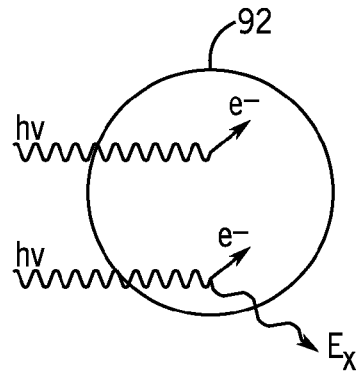
FIGS. 8-13 generally illustrate various interaction effects of electromagnetic energy with a scintillation crystal and impacts on the deposited spectrum.
Figure 9:
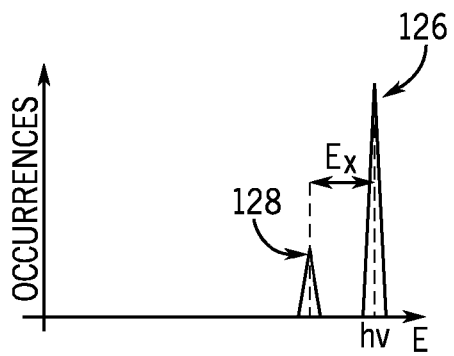

In the case of photoelectric absorption generally depicted in FIG. 8, the incident gamma-ray (or x-ray) interacts with an electron of an atom of the scintillation crystal 92 (e.g., an electron of the inner electron shell (K-shell) of the atom) and disappears by giving up its energy hv. An electron (e$^-$) is produced from this interaction (i.e., ejected from the atom receiving the incident gamma-ray or x-ray) along with either an x-ray photon or a so-called Auger electron following electron rearrangement due to the vacancy left by the ejected electron. For atomic numbers Z>39, the probability of generating an x-ray photon is greater than seventy percent and increases with Z. The incident photon energy is often fully deposited in the detector (as is the case with the upper incident ray in FIG. 8), thus contributing to a full-energy peak 126 as depicted in FIG. 9. However, if the effect takes place near the detector surface, an x-ray photon of energy $E_X$ may leave the detector (as is the case with the lower incident ray in FIG. 8). The deposited energy will then be hv−$E_X$, corresponding to a characteristic x-ray escape peak (EP) 128 in the spectrum shown in FIG. 9.

Figure 10:
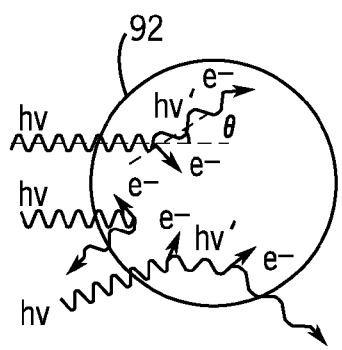

As generally shown in FIG. 10, in the case of Compton scattering the incident gamma-ray (or x-ray) with energy hv interacts with an electron by giving up part of its energy to the electron itself and being scattered at an angle θ. The portion of energy between the recoil electron and the scattered photon of energy hv'≤hv depends on the scattering angle θ. When both Compton scattering products deposit their energy in the detector (when the scattered photon is eventually photoelectric-absorbed as is the case with the uppermost incident ray in FIG. 10), the incident photon contributes to the full-energy peak 126 depicted in FIG. 11. But when the scattered photon leaves the detector (see, e.g., the middle incident ray in FIG. 10), just the recoil electron energy is deposited. The maximum recoil electron energy corresponds to a head-on collision, i.e., θ=π, and is given by:

$$E_{e^-,\theta=\pi} = hv \frac{2hv/m_0 c^2}{1 + 2hv/m_0 c^2}$$

Figure 11:
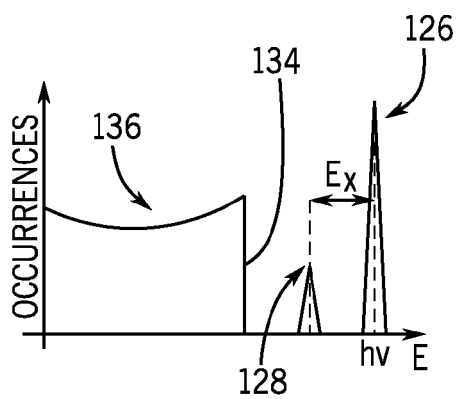

In the spectrum of FIG. 11, this is represented by the Compton edge (CE) 134 at energy $E_{e^-,\theta=\pi}$ and, for 0≤θ≤π, recoil electrons generate to the so-called Compton continuum 136. Moreover, if a scattered photon escapes the detector after multiple Compton scatterings (see, e.g., the lowermost incident ray in FIG. 10), the deposited energy will be ε<$E_e$−<hv−ε, with ε≅0, thus leading to an extra background overlapping the Compton continuum for energies less than or equal to $E_{e^-,\theta=\pi}$ (which, for the sake of clarity, is not shown in FIG. 11).

Figure 12:
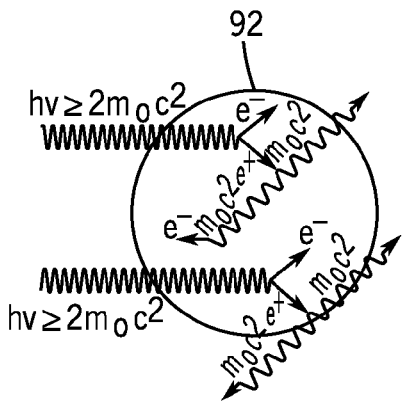
Figure 13:
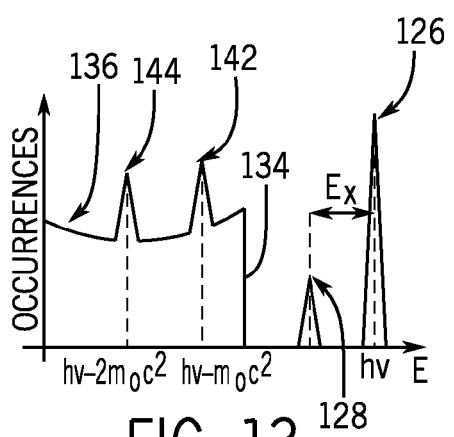

Unlike the previous interaction effects, pair production is a threshold effect. In such an interaction (two of which are generally depicted in FIG. 12) a gamma-ray with energy hv disappears to create an electron-positron pair. Since the electron (and positron) rest mass $m_0$ corresponds to an energy of $m_0 c^2$=511 keV, the pair creation can take place just if hv≥2 $m_0 c^2$. In some instances, the annihilation photons from positron-electron annihilation (e$^+$ are highly unstable particles) deposit their whole energies in the detector, thus contributing to the full-energy peak 126 in FIG. 13. In other instances, however, either one or both photons can leave the detector. This leads to the formation of single and double escape peaks 142 and 144 located in the spectrum at hv−$m_0 c^2$ and hv−2 $m_0 c^2$, respectively.

Escape peak intensities and Compton continuum shape may be empirically determined for emissions at a particular energy level with a given detector size and hardware geometry. In the more general scenario of several gamma-ray or x-ray emissions of different energies to be detected, however, such empirical determination becomes increasingly difficult. Even an analytical approach may not provide desired results. For example, on determining the Compton continuum, the Klein-Nishina equation does not provide an accurate quantitative description of the continuum because, among other things, its free electron hypothesis is unrealistic.

In at least some embodiments of the present disclosure, the complex problem of incident photon recovery from an energy spectrum is represented by Monte Carlo codes, where a combination of nuclear physics and statistics allows an accurate description of radiation-matter interactions. The Monte Carlo N-Particle (MCNP) transport code, developed by and available from Los Alamos National Laboratory of the United States, is used in at least some embodiments to simulate the response of the scintillation crystal 92 to electromagnetic radiation of different energies, although other codes or algorithms could be used for this simulation in different embodiments (e.g., Geant 4 from the European Organization for Nuclear Research (CERN)). Once characteristics of the three-dimensional hardware geometry, the radiation source, and the detector are introduced, MCNP takes into account detector-related effects and also simulates gamma-ray interactions with materials surrounding the detector itself. The result is a description of an ideal crystal response function (CRF).

Figure 14:
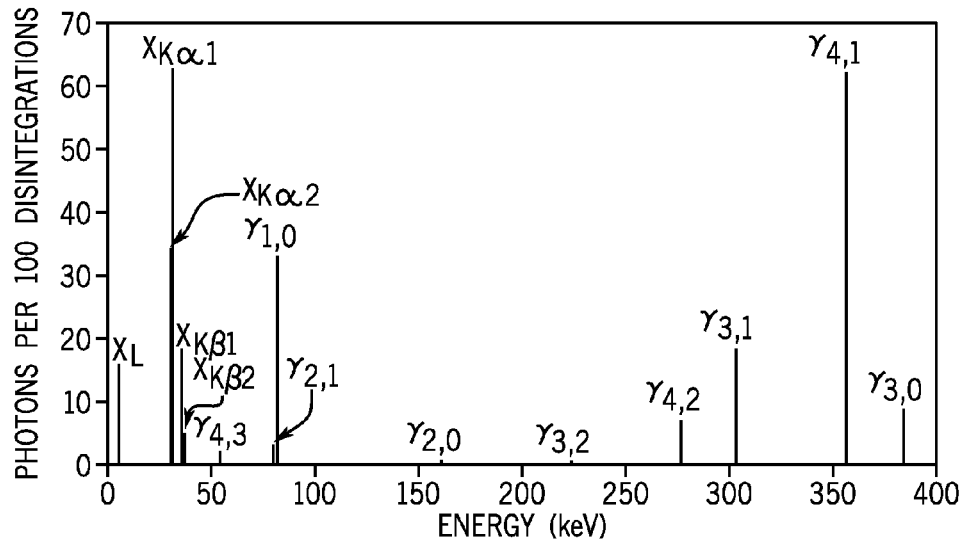
FIG. 14 depicts electromagnetic emissions of barium-133 at various energy levels.
Figure 15:
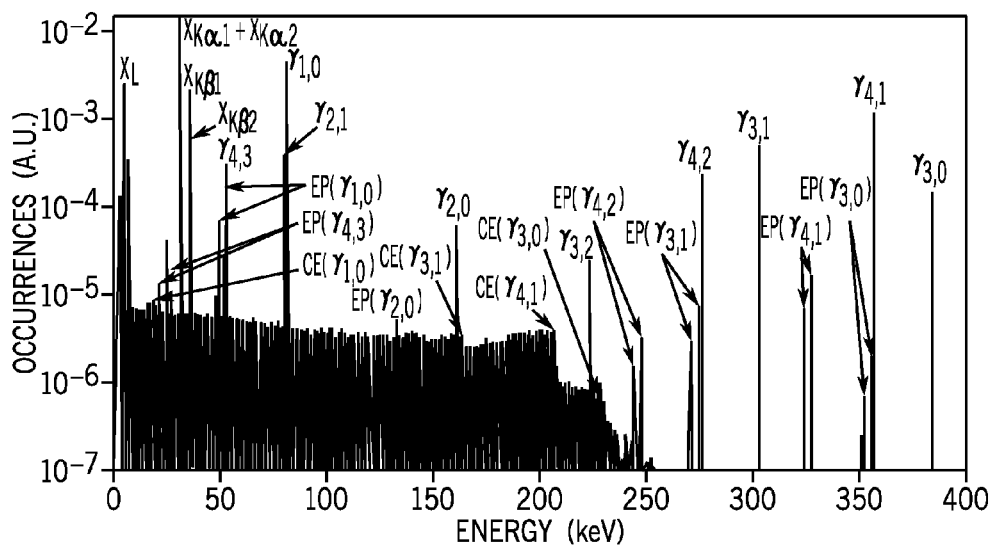
FIG. 15 depicts a simulated crystal response function in accordance with one embodiment.

By way of example, FIG. 14 shows an x-ray and gamma-ray emission spectrum of barium-133 and FIG. 15 illustrates an ideal CRF of a 7-mm thick inorganic scintillation crystal to the barium-133 radiation as simulated by MCNP. Spectral components in both of these figures are labeled with their respective generation mechanism. Although the spectrum shown in FIG. 15 is single- and double-escape peak free (as the most energetic emission from barium-133 occurs at 383.8 keV, which is less than 2 $m_0c^2$), the cumulative interactive effects due to the finite detector size make the spectrum complicated, with many high energy photons sorted in low energy bins.

Figure 16:
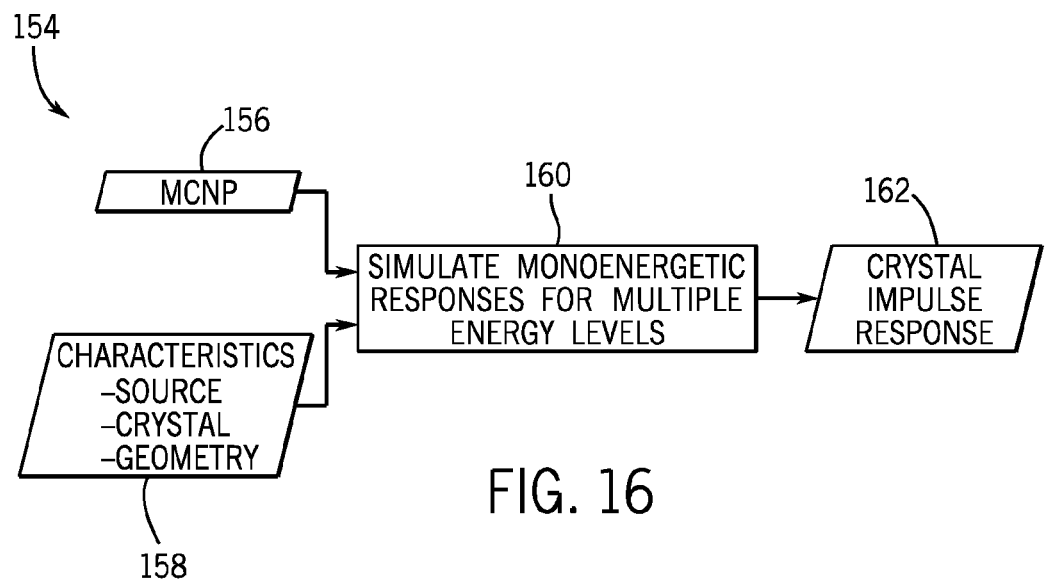
FIG. 16 generally depicts determination of a crystal impulse response for a scintillation crystal in accordance with one embodiment.

One embodiment for modeling the impulse response of a scintillation crystal is generally depicted by flow chart 154 of FIG. 16. In order to single out the spectral contribution of each barium-133 emission, the CRF can be simulated for one emission at a time. More specifically, using MCNP 156 and various characteristics 158 of the apparatus (such as characteristics of the radiation source, the detector, and the three-dimensional hardware geometry, as discussed above), monoenergetic responses for multiple energy levels can be simulated (block 160) to generate a set of monoenergetic CRFs that characterize the crystal impulse response 162. The simulation of the monoenergetic responses can be performed with MCNP or in any other suitable manner. Moreover, as detailed below, this set of monoenergetic CRFs facilitates later determination of the detector incident photons from a measured spectrum.

As the energy deposition process is an energy-varying linear system, the crystal response function is fully characterized by its impulse response h(e', e). Consequently, the deposited spectrum can be computed from the convolution product of the incident spectrum with h(e', e):

$$d(e)=\int i(e')h(e',e)de'$$

This convolution product can also be expressed in a matrix form. If H denotes the energy deposition matrix into the scintillation crystal, $H_{ij}$=h($e_i$,$e_j$), obtained from MCNP (or other) simulations; I refers to the incident spectrum vector, $I_k$=i($e_k$); and D denotes the deposited spectrum vector, $D_k$=d($e_k$), then the convolution equation can also be written in discretized form as:

$$D=H \cdot I$$

Figure 17:
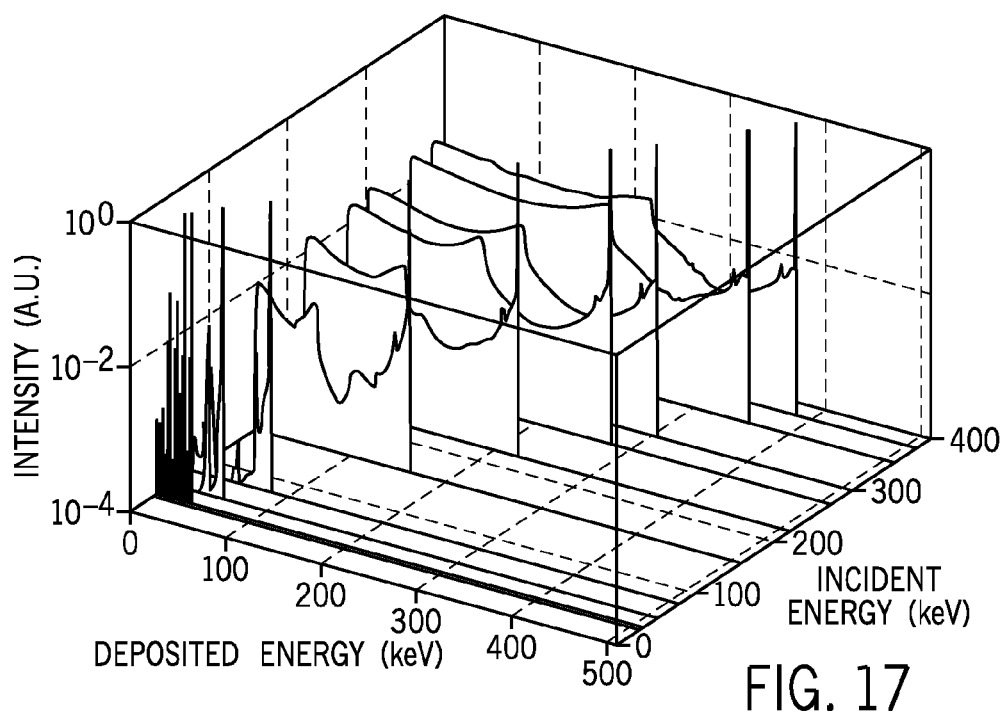
FIG. 17 depicts simulated individual spectral responses of a scintillation crystal for various incident energy levels in accordance with one embodiment.

The crystal response matrix H contains the individual responses to source emissions, such as from barium-133 as discussed above. These individual responses of H (for the example of barium-133 source emissions) are generally depicted in FIG. 17. Particularly, FIG. 17 depicts the simulated spectral responses of the crystal for various energy levels of incident electromagnetic radiation corresponding to the gamma-ray and K x-ray spectral components of FIG. 14. In the present example, these spectral responses are for ten incident energy levels of interest (rounded to the nearest keV): 31 keV, 35 keV, 53 keV, 81 keV, 161 keV, 223 keV, 276 keV, 303 keV, 356 keV, and 384 keV. In other instances, however, the incident energy levels for which the response is simulated could differ from the preceding example. Further, monoenergetic responses could be simulated for a greater or lesser number of incident energy levels in accordance with the present techniques.

Determining the PMT response function at block 114 of FIG. 7 includes determining a PMT response function g(e', e) that relates the deposited spectrum d(e) to a smeared spectrum s(e). While here described as a PMT response function for explanatory purposes, it is noted that a solid-state detector that does not have a PMT could also be similarly modeled. In the case of solid-state detectors, the smearing effect would result from the charge collection process rather than the electron multiplication process noted below.

Figure 18:
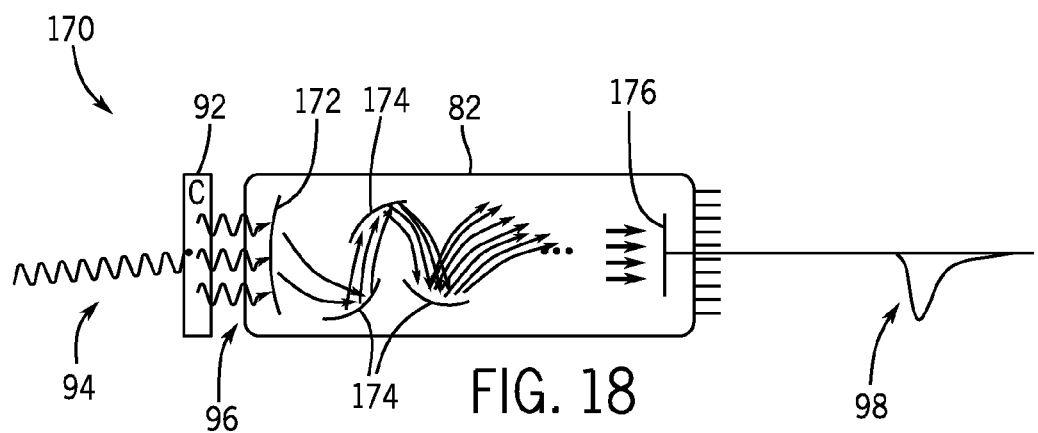
FIG. 18 generally illustrates additional details of the photomultiplier tube of FIG. 6 in accordance with one embodiment.

Additional details of a PMT 82 are generally illustrated in diagram 170 of FIG. 18 in accordance with one embodiment. As previously noted, the scintillation crystal 92 converts incident radiation 94 into pulses of light 96, which is measured and converted into electrical signals 98 by the PMT 82. As depicted in the present figure, photons of light 96 from the scintillation crystal 92 fall on a light-sensitive layer in the form of a photocathode 172, causing the photocathode to emit photoelectrons. These photoelectrons are focused electrostatically onto a series of dynodes 174 that progressively amplify the current associated with the emitted photoelectrons. The amplified signal is collected at an anode 176 in the form of current pulses 98 (which can be passed to the amplifier 84 as described above).

Due to the statistical nature of the electron multiplication process of PMTs, the output charge can vary from one event to the other. This uncertainty follows a Poisson process which results in a spectral broadening (i.e., smearing) of the ideal CRF Dirac peaks. This spectral broadening can be approximated by a Gaussian filter whose parameters will depend on the crystal-PMT linearity and resolution. A photon depositing in the crystal the energy $e_j$ will be recorded in average at the channel $\mu(e_j)$ with a standard deviation $\sigma(e_j)$. These two functions (which are energy and resolution response models) are specific to each detector assembly (more specifically, the crystal-PMT assembly in those embodiments using a crystal scintillator) and can be parameterized the following way or based on any other energy relationship:

$$\mu(e_j)=p(1)e_j+p(2)$$

$$\sigma(e_j)=p(3)\sqrt{e_j}+p(4)$$

In some embodiments, the parameters p(1), p(2), p(3), and p(4) are adjusted continuously in real time to account for temperature or aging drifts that may occur over a detector's lifetime. In other embodiments, these parameters are adjusted continually, such as periodically at any specified frequency (e.g., once per minute).

As it is an energy-varying linear system, the PMT response function is fully characterized by its impulse response g(e', e). The smeared spectrum can therefore be computed from the convolution product of the deposited spectrum with g(e', e):

$$s(e)=\int d(e')g(e',e)de'$$

This convolution product can also be expressed in a matrix form. For example, if G(P) is a Gaussian matrix, $g_{ij}$=g($e_i$,$e_j$), based on the energy and resolution response models above; D is the deposited spectrum vector, $D_k$=d($e_k$); and S is the smeared spectrum vector, $S_k$=s($e_k$), then the convolution equation can be written in discretized form as:

$$S=G(P) \cdot D$$

Figure 19:
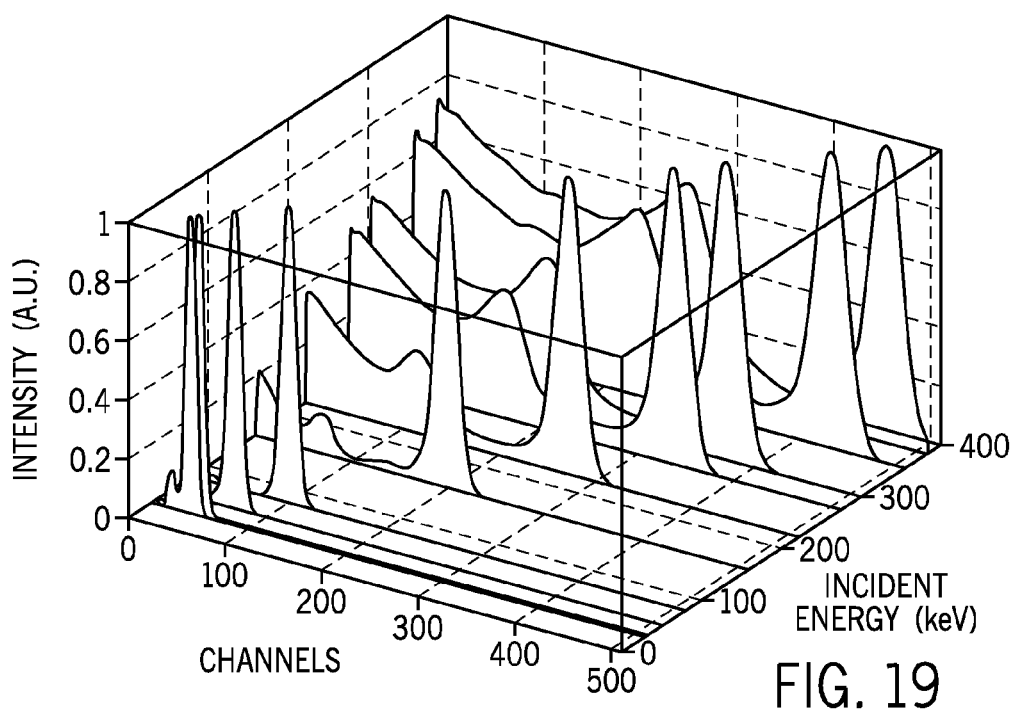
FIG. 19 depicts deconvolution kernel components based on the individual spectral responses of FIG. 17 in accordance with one embodiment.

The product matrix G(P)H can be referred to as the deconvolution kernel. This deconvolution kernel characterizes the impulse response of the scintillation crystal 92 and the PMT 82. The deconvolution kernel also contains the single energy spectra (components) from which observed spectrums are created. These single energy spectra are generally depicted in FIG. 19, and it is noted that each depicted spectrum is a smeared version of an associated spectrum depicted in FIG. 17.

Returning again briefly to FIG. 7, determining the amplifier response function at block 116 includes determining an amplifier response function $f$ which relates the smeared spectrum s(e) to an observed spectrum o(e). Each output of the PMT 82 described above is, in essence, an amount of electrical charge proportional to the amount of energy in a photon (e.g., a gamma-ray or x-ray photon) deposited in the scintillation crystal 92. Electrical components, such as the amplifier 84 and a multi-channel analyzer, then collect that charge, measure its amplitude, and store it in the spectrum.

Figure 20:
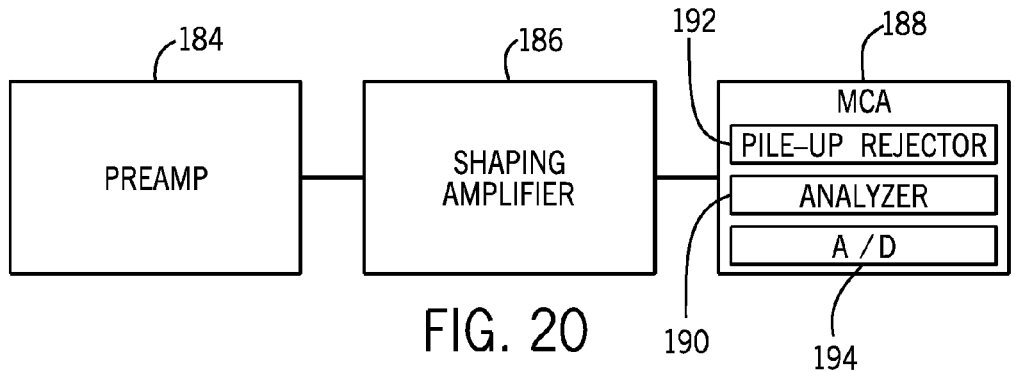
FIG. 20 is a block diagram of electronic components of the apparatus of FIG. 1 in accordance with one embodiment.

One example of such components is shown in FIG. 20. In this embodiment, the electrical components include a preamplifier 184, a shaping amplifier 186, and a multi-channel analyzer (MCA) 188. The preamplifier 184 and the shaping amplifier 186 may be components of the amplifier 84 (FIG. 6), while the MCA 188 can be included as part of the detector 16, part of the computer 22 (e.g., as an input device 46), or as a separate component. The preamplifier 184 converts and amplifies the current pulses 98 it receives from the PMT 82 into voltage pulses. The shaping amplifier 186 transforms these voltage pulses into linear pulses, such as unipolar or bipolar semi-Gaussian pulses, having faster baseline restoration and better signal-to-noise ratio.

The multi-channel analyzer 188 includes analyzer circuitry 190 for sorting the linear pulses into respective channels. The MCA 188 could include any suitable number of measurement channels for sorting linear pulses received from the shaping amplifier 186. For example, in some embodiments the MCA 188 has 512 channels or 1024 channels. When two incident photons arrive at the detector within the width of the shaping amplifier output pulse, their respective pulses pile up to form an output pulse of distorted height, leading to a distorted energy spectrum. While post-processing algorithms may be able to describe the effect of pulse pile-up on the spectrum in some instances, they can also be too resource-intensive (e.g., in CPU processing cycles) for certain (e.g., real-time) implementations.

Accordingly, the depicted MCA 188 includes a pile-up rejector 192. This pile-up rejector 192 discards pile-up events in which their time interval is longer than a threshold pile-up rejection time. The threshold pile-up rejection time can be set to any desired level, such as a level that would result in the discarding of most pile-up events. This can simplify the interpretation of the spectrum distortion by generally reducing pile-up effects to the case of synchronous pulses. In order to model the distortion due to these left-over synchronous pulses, a quantitative analysis is performed on each channel k of the spectrum. It is possible to demonstrate from Poisson's law that the probability of two photons piling-up is:

$$P_0 = n_{tot}\tau\exp(-n_{tot}\tau),$$

where $\tau$ is the pile-up rejection time and $n_{tot}$ is the total count rate.

Figure 21:
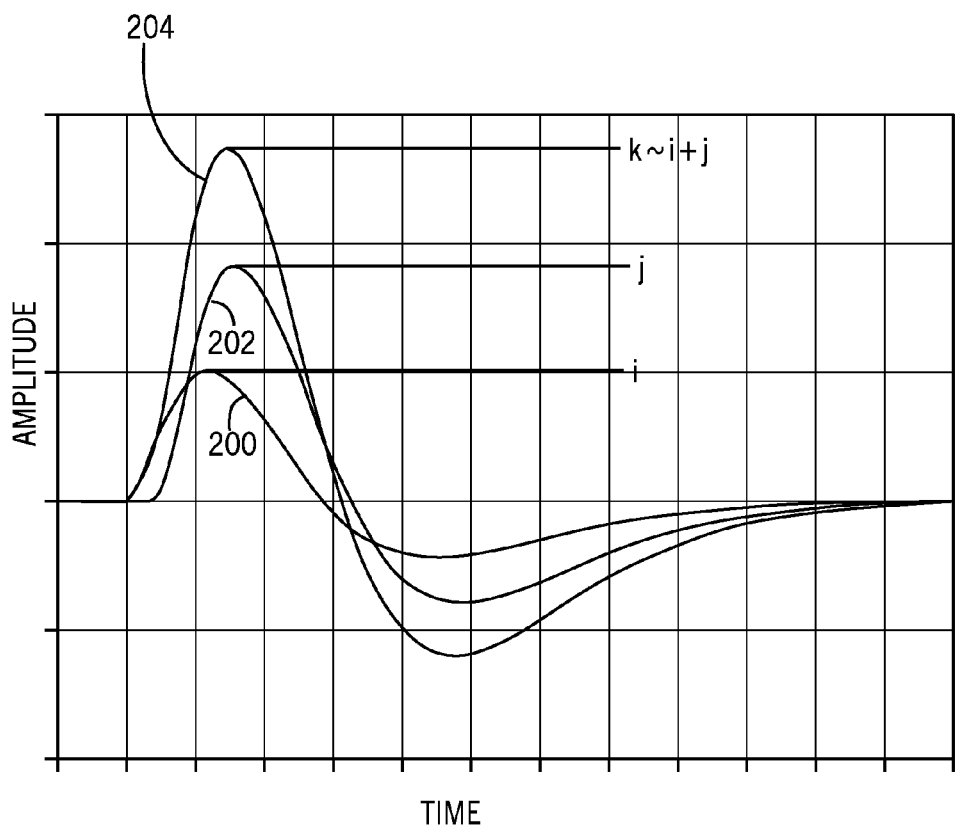
FIG. 21 is a graph generally depicting synchronous pulses generated by the photomultiplier tube in accordance with one embodiment.

An example of synchronous pulses is generally represented in the graph of FIG. 21, in which a pulse 200 (with amplitude i) is synchronous with a pulse 202 (with amplitude j), resulting in a cumulative pulse 204 that would be read into a channel k due to the summation of i and j. Further, if i and j denote the incident amplitude combinations, the gains and losses rates can be calculated for each channel k via the following formula:

$$G_k = n_{tot}\sum_{i=1}^{k-1} P_i P_{k-i} P_0$$

with $P_k = \dfrac{S_k}{n_{tot}}$ $$L_k = 2n_{tot}\sum_{i=1}^{n_{tot}} P_i P_k P_0$$

The observed spectrum is then a balance of gains and losses in each channel:

$$O_k = f(S_k) = S_k - L_k + G_k$$

Each part of the detection chain has been modeled above in the form of individual response functions. The global detector response can be considered a physical model that combines those individual response functions to represent the functioning of the modeled detector chain. Consequently, this global detector response can be expressed in matrix form as:

$$O = f(G(P)H \, I)$$

In at least some embodiments, this physical model for detector response is used to infer incident count rates for photons of different energy levels received by the detector 16. The inferred count rates can then be used to determine characteristics of an analyzed fluid. One example of a process for inferring the incident count rates and then characterizing a fluid based on the inferred count rates is generally represented by flow chart 210 in FIG. 22. In this embodiment, electromagnetic radiation (e.g., x-rays and gamma rays from emitter 14) is transmitted (block 212) through a fluid of interest. The fluid attenuates the radiation such that a portion of the radiation is received (block 214) at a detector (e.g., detector 16). At block 216, the energy spectrum of the radiation received by the detector is measured, which may be performed by a multi-channel analyzer such as that described above. In at least some instances, the full energy spectrum of the received radiation is measured. In others, a partial energy spectrum can be measured, such as a portion of the energy spectrum falling within a contiguous range of multiple channels of a multi-channel analyzer. But it is noted that, as used herein, measurement of the energy spectrum (whether a full energy spectrum or a partial energy spectrum) means measurement of counts within numerous channels of a multi-channel analyzer, rather than merely measuring counts in a handful of channels (e.g., two to ten channels isolated from one another) corresponding to particular energy levels of interest. This measurement of the spectrum, rather than of a small number of individual channels, allows incident count rates to be inferred from the measured energy spectrum in accordance with the present techniques.

At block 218, the measured energy spectrum and the physical model for detector response are used to infer variables of the physical model. For the model described above, inputs of the model include crystal monoenergetic responses H and the detector energy and resolution functions $\mu(e)$ and $\sigma(e)$, and the variables include the incident count rates for photons of different energy levels and the detector-specific parameters p(1), p(2), p(3), and p(4). These variables can be inferred through a deconvolution process based on the detector response function O.

More specifically, in at least some instances the detector response function of the physical model is compared to the measured energy spectrum, which may include performing optimization (e.g., least squares optimization) on the detector response function to fit the detector response function to the measured energy spectrum and infer the incident count rates and detector-specific parameters. For example, letting Y be the measured spectrum, a non-linear least squares algorithm can be used to determine the detector-specific parameters P and the incident count rates I that minimize the following residuals:

$$\left\|\frac{Y-O}{\sigma_Y}\right\|^2 \Leftrightarrow \left\|\frac{Y-f(G(P)HI)}{\sqrt{Y}}\right\|^2$$

The residuals can be weighted by the standard deviation of the measurements, i.e., the square root of counts in this case since counting processes are ordinarily assumed to follow Poisson statistics. A Levenberg-Marquardt algorithm can be used to perform the optimization (in the form of least squares minimization) or a simpler Gauss-Newton technique can be used. Still further, maximum likelihood or maximum entropy methods can be used to perform the optimization, as can any other suitable methods.

Once the incident count rates I are inferred, these count rates can be compared with empty pipe count rates to determine the attenuation of electromagnetic radiation by the analyzed fluid for multiple energy levels, as described above with respect to FIG. 4. The determined attenuation can then be used to characterize the fluid (block 220), such as by determining phase fractions for the fluid or information about some additional component, such as hydrogen sulfide or salts in the fluid, as discussed below. Further, the inferred detector-specific parameters P can be used to calibrate the detector (block 222), such as to maintain the spectral output of the detector at a reference position.

Figures 22, 23:
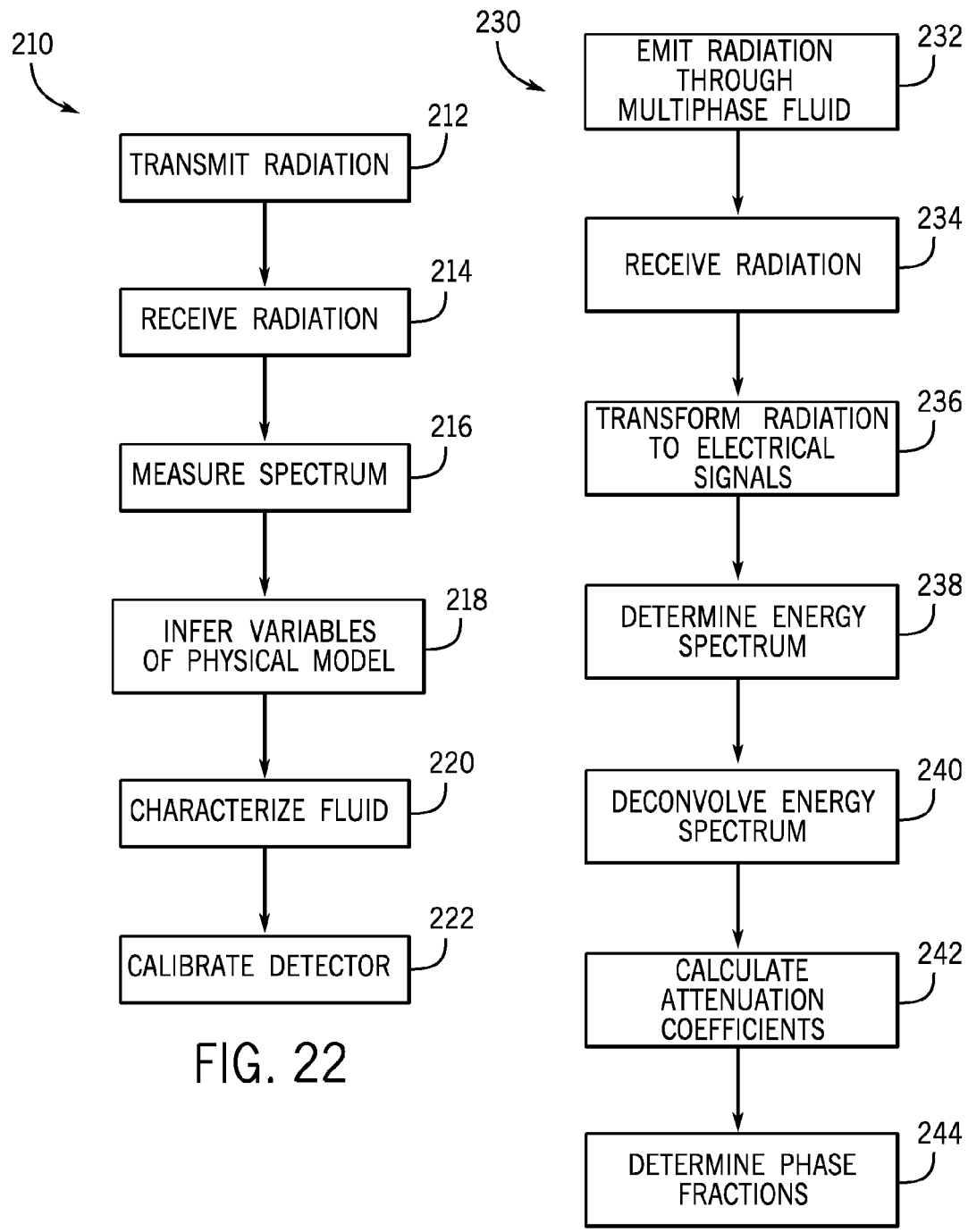
FIG. 22 is a flow chart for inferring incident count rates using a physical model of a detector in accordance with one embodiment.
FIG. 23 is a flow chart for determining phase fractions of a fluid through spectrum deconvolution in accordance with one embodiment.

In accordance with another embodiment, a process for determining phase fractions of a multiphase fluid is generally represented by flow chart 230 in FIG. 23. In this embodiment, electromagnetic radiation is emitted (block 232) through a multiphase fluid. For instance, a radioactive source can emit x-rays and gamma rays into a multiphase fluid flowing through a fluid conduit. The radiation incident on a detector is received (block 234) and transformed (block 236) into electrical signals as described above. It will be appreciated that the electrical signals are representative of the incident radiation.

An energy spectrum is determined (block 238) from the electrical signals and then deconvolved (block 240) to estimate quantities of photons of multiple energy levels received by the detector. The deconvolution of the determined energy spectrum (which in at least some instances is the full energy spectrum of the received radiation) can be performed in any suitable manner, such as by fitting a modeled detector response function in the manner described above. Attenuation coefficients for the fluid can be calculated (block 242) and phase fractions can be determined (block 244) based on the attenuation coefficients as described elsewhere herein. The phase fractions in some embodiments include gas, water, and oil phases. Further, the phase fractions could include other components in addition to (or in place of) gas, water, and oil. Still further, information about additional components, such as hydrogen sulfide or salts, could also be determined, as described below.

Figure 24:
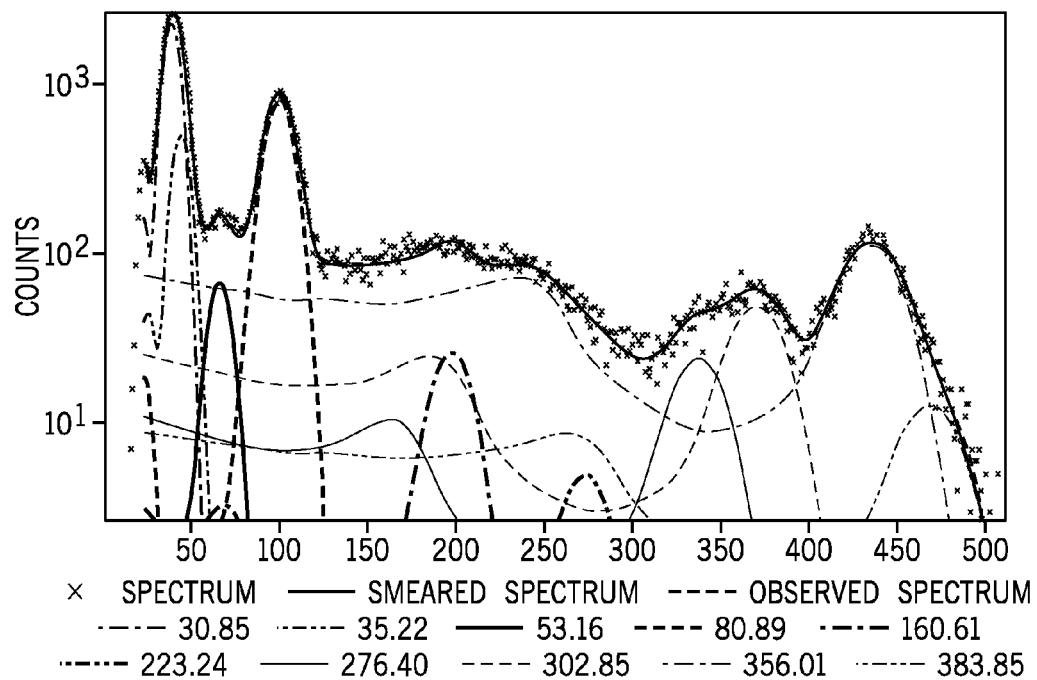
FIGS. 24-27 are examples of spectrum deconvolutions for various radioactive sources and detector types in accordance with certain embodiments.
Figure 25:
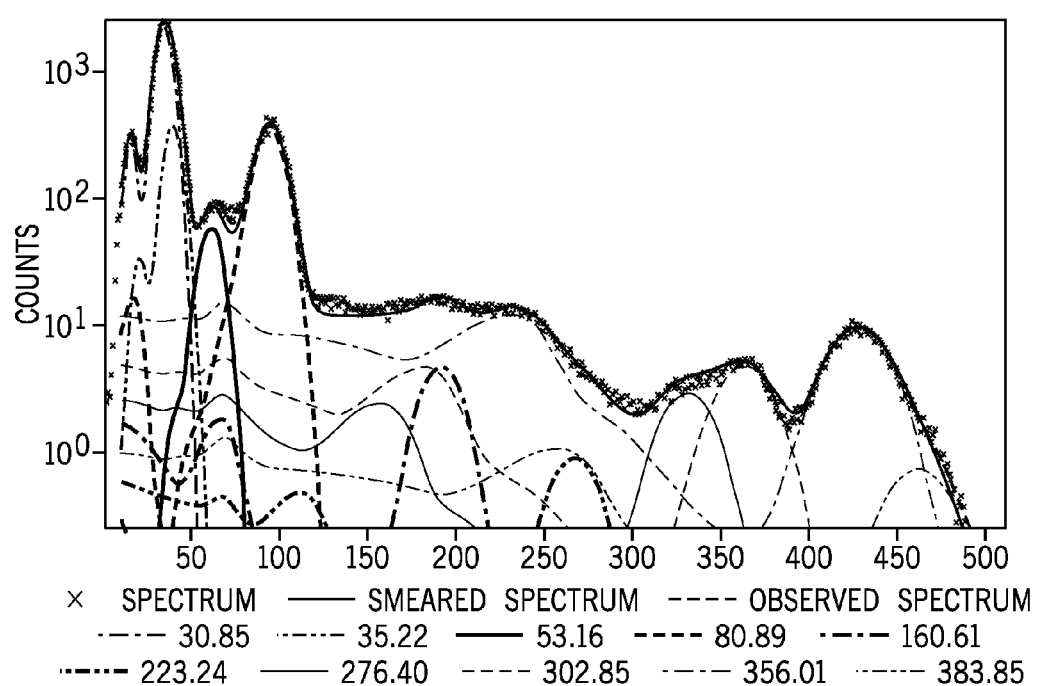
Figure 26:
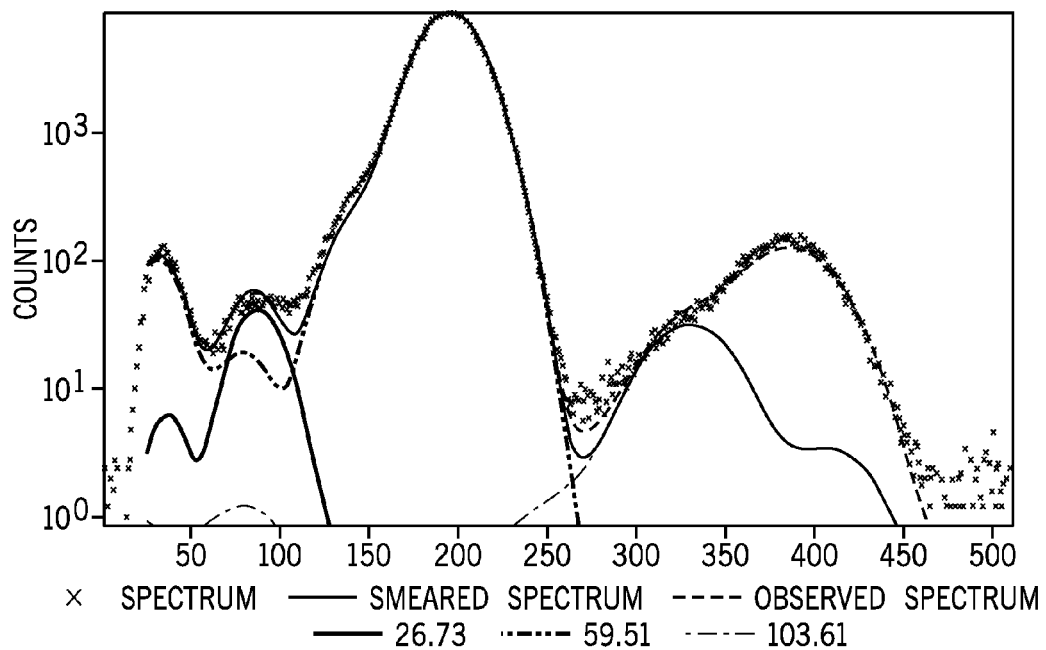
Figure 27:
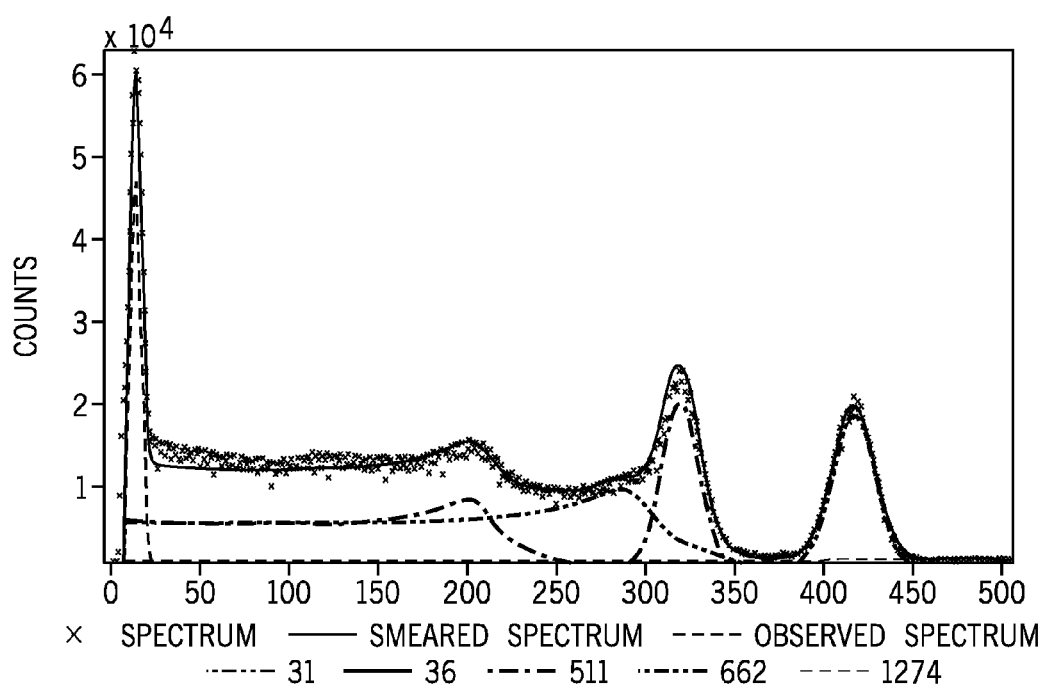

Examples of spectrum deconvolutions for various radioactive sources and detector types are generally depicted in FIGS. 24-27. In each of these examples, the deconvolution kernel is computed from MCNP simulations based on input characteristics of the radioactive source, the detector, and source-detector geometry. Further, each of these graphs depicts incident photon counts (y-axis) over 512 channels (x-axis). In addition to a measured spectrum, an observed spectrum, and a smeared spectrum, individual spectral components associated with energy lines of the respective radioactive source are also depicted (with the source energy lines enumerated in keV in at the bottom of each of these figures). The data depicted in FIG. 24 is based on a barium-133 radiation source and a 10 mm inorganic scintillation crystal. In FIG. 25, the depicted data is also based on a barium-133 radiation source, but with a 2 mm inorganic scintillation crystal. In FIG. 26, the depicted data is based on an americium-241 radiation source and a 10 mm scintillator. And the data in FIG. 27 is based on radiation source having cesium-137 and sodium-22 with a 25.4 mm (one-inch) inorganic scintillation crystal.

A further example of a process for calculating incident count rates, attenuation, and phase fractions of a fluid is generally represented by flow chart 250 in FIG. 28. In this embodiment, photons of different energies that have passed through a fluid of interest (e.g., a multiphase fluid in a conduit) are received at a detector (block 252) and the energy spectrum of the received photons is then measured (block 254). Spectral components of the measured energy spectrum are derived (block 256) for multiple energy levels of the photons received by the detector. These spectral components can be derived in any suitable manner, including using multiple monoenergetic response functions in the manner described above. Count rates can then be measured (block 258) for at least two energy levels of the received photons based on the derived spectral components. The at least two energy levels can include any energy levels of interest. For example, the received photons can include x-ray photons and gamma-ray photons, and the at least two energy levels can include a first energy level for received x-ray photons and a second energy level for received gamma-ray photons. In some embodiments, such as those using a barium-133 source, the first energy level of received x-ray photons is between 30 keV and 36 keV and the second energy level of received gamma-ray photons is between 79 keV and 81 keV. Attenuation rates of the photons by the fluid for the at least two energy levels and phase fractions for the fluid can then be calculated at blocks 260 and 262 in any suitable manner.

Additionally, an example of a process that optimizes variables of a detector response model to enable calculation of fluid characteristics is generally represented by flow chart 270 in FIG. 29. In this embodiment, electromagnetic radiation is transmitted through a fluid (block 272) and an attenuated portion of that radiation is received at a scintillation crystal of a detector (block 274). The scintillation crystal emits light in response to the received radiation, and this light is received by a photomultiplier tube (block 276). The light is converted to electrical signals (block 278) to enable measurement of the energy spectrum generated by the radiation received at the scintillation crystal (block 280). Variables of a detector response model can then be optimized, as described above, to minimize residuals between the measured energy spectrum and an output of the detector response model (block 282). The optimized variables of the detector response model can include incident count rates for different energy levels of photons received by the scintillation detector and detector-specific parameters, as also described above. In some embodiments, the residuals are weighted based on a standard deviation of the measured energy spectrum and the variables are optimized with a non-linear, least squares algorithm, such as a Levenberg-Marquardt algorithm or a Gauss-Newton algorithm. Further, attenuation coefficients of the fluid for the different energy levels of radiation and phase proportions (e.g., for water, oil, and gas) can be calculated (blocks 284 and 286).

While the present techniques can be used to determine fractional portions for a multiphase fluid having three components (e.g., oil, water, and gas), they can also be used to determine additional components of the multiphase fluid. In some instances, the present techniques can be applied to cases of fluids having a combination of hydrocarbon liquid (e.g., oil), water, hydrocarbon gas, and some additional component, e.g., hydrogen sulfide or salts. With the present techniques, count rates from distinct energy levels in the electromagnetic radiation from the emitter 14 can be inferred. This can give as many equations as the number of the energy levels, thus providing a system of linear equations that can be inverted to calculate the fractional components of oil, water and gas as well as further information related to additional components, for instance in the form of change of salt and hydrogen sulfide quantity. The equations regarding the additional components will involve count rates of extra energy levels as well as other physical quantities depending on the chemical behavior of the additional components with oil, water and gas.

Measurement of the full spectrum with the deconvolution process also enables monitoring the detector's health status in real-time. The detector status may be monitored by observing the deconvolution spectrum and detector parameters in real-time and comparing them to expected values under the same or similar conditions. For example, the observed full spectrum may exhibit characteristics different than those expected in various areas. Such as, the full spectrum may show peaks at different channels or peaks at different intensities, or even a different number of peaks, e.g. 3 peaks shown when 4 peaks are expected. Similarly, the detector parameters may exhibit different data points than expected or would be observed under normal circumstances. Automated controls can be used to ensure that measurement efficiency is maintained via feedback control loops. Besides ensuring the long-term stability of the measurement, the full spectrum deconvolution technique also significantly reduces and in some instances eliminates the use of thermal control of the detector system. In other words, the full spectrum measurement and deconvolution technique enable a MPFM that is more self-regulated based on the measured responses. This makes it possible to use a simpler system, operated at ambient conditions while providing excellent measurement stability and consistency.

From the above description, it will be appreciated that the present disclosure introduces a method of determining phase fractions for a multiphase fluid, the method comprising: receiving electromagnetic radiation transmitted through the multiphase fluid and incident on an electromagnetic radiation detector; transforming the incident electromagnetic radiation to electrical signals representative of the incident electromagnetic radiation; determining an energy spectrum from the electrical signals; deconvolving the determined energy spectrum to estimate quantities of photons of at least two different energy levels in the electromagnetic radiation that are received by the electromagnetic radiation detector; calculating attenuation coefficients for phases of the multiphase fluid for the at least two different energy levels based on the estimated quantities of photons of the at least two different energy levels received by the electromagnetic radiation detector; and determining the phase fractions for the phases of the multiphase fluid based on the calculated attenuation coefficients. In some embodiments, deconvolving the determined energy spectrum includes fitting a modeled detector response function to the determined energy spectrum. Further, in at least one embodiment, deconvolving the determined energy spectrum includes fitting a modeled detector response function having a deconvolution kernel that characterizes the impulse response of one or more components of the electromagnetic radiation detector. Determining the phase fractions for the phases of the multiphase fluid can include determining the phase fractions for a gaseous phase, an aqueous liquid phase, and an oily liquid phase of the multiphase fluid. Also, calculating the attenuation coefficients for the phases of the multiphase fluid can include comparing the estimated quantities of photons of the at least two different energy levels with estimated quantities of photons of the at least two different energy levels emitted from a source of the electromagnetic radiation. Further still, transforming the incident electromagnetic radiation to the electrical signals can include transforming gamma radiation to the electrical signals. And the method can also comprise emitting the electromagnetic radiation from a radioactive source through the multiphase fluid as it flows through a flow meter.

It will be further appreciated that the present disclosure introduces a device comprising a non-transitory, computer-readable storage medium encoded with application instructions that, when executed by a processor, enable: receiving a measured spectrum representative of electromagnetic radiation incident on a detector; fitting a modeled spectrum to the measured spectrum; and determining from the modeled spectrum count rates for photons of the electromagnetic radiation incident on the detector. In one embodiment, fitting the modeled spectrum to the measured spectrum includes minimizing residuals between the measured spectrum and the modeled spectrum. The non-transitory, computer-readable storage medium can be further encoded with application instructions that, when executed by the processor, enable calculation of phase fractions of a multiphase fluid based on the determined count rates in at least some embodiments. In some instances, the device is a memory device or a computer having the processor and the non-transitory, computer-readable storage medium. Further, in at least one embodiment, such a computer is a flow computer of a multiphase flow meter.

The present disclosure also introduces an apparatus comprising: a fluid conduit; a radioactive source coupled to the fluid conduit; a sensor coupled to the fluid conduit and configured to receive electromagnetic radiation from the radioactive source, measure the energy spectrum of the received electromagnetic radiation, and output data indicative of the measured energy spectrum; and a controller operable to receive the output data from the sensor and to determine, through deconvolution of the measured energy spectrum, count rates for photons of different energy levels in the electromagnetic radiation received by the sensor. The controller in some embodiments is a flow computer of a multiphase flow meter. The radioactive source can emit gamma radiation and the detector can be configured to detect the gamma radiation. Further, the radioactive source can also emit x-rays and the detector can be configured to detect the x-rays. In some embodiments, the radioactive source includes barium-133. Also, in at least some instances the detector of the apparatus includes a scintillator.

Further yet, the present disclosure introduces a method comprising: transmitting electromagnetic radiation from a source through a fluid in a conduit; receiving an attenuated portion of the electromagnetic radiation at a scintillation crystal of a detector; receiving, at a photomultiplier tube of the detector, light emitted from the scintillation crystal in response to receipt of the attenuated portion of the electromagnetic radiation received at the scintillation crystal; converting the light received at the photomultiplier tube into electrical signals; measuring, based on the electrical signals, an energy spectrum generated by the attenuated portion of the electromagnetic radiation; and optimizing variables of a response model for the detector to minimize residuals between the measured energy spectrum and an output of the response model, wherein the optimized variables include incident count rates for different energy levels of photons received by the scintillation crystal and detector-specific parameters. This method can also include using at least two of the optimized incident count rates to calculate attenuation coefficients of the fluid for at least two of the different energy levels. Further, in one embodiment the method includes measuring the salinity of the fluid based on at least two of the optimized incident count rates. In some instances, the method also includes calculating the proportions of water, oil, and gas in the fluid based on the calculated attenuation coefficients. Optimizing the variables of the response model to minimize the residuals can include weighting the residuals with a standard deviation of the measured energy spectrum. Also, optimizing the variables of the response model can include optimizing the variables with a non-linear, least squares algorithm. In at least some embodiments, optimizing the variables with a non-linear, least squares algorithm includes optimizing the variables with a Levenberg-Marquardt algorithm or a Gauss-Newton algorithm.

Additionally, the present disclosure introduces a method comprising modeling a response function of a detector assembly to electromagnetic radiation, the detector assembly having a scintillation crystal, a photomultiplier tube, and an amplifier, wherein modeling the response function of the detector assembly includes: determining a crystal response function that relates an electromagnetic spectrum incident on the scintillation crystal of the detector assembly to an electromagnetic spectrum deposited in the scintillation crystal of the detector assembly; determining a photomultiplier tube response function that relates the electromagnetic spectrum deposited in the scintillation crystal to a smeared spectrum; and determining an amplifier response function that relates the smeared spectrum to an observed spectrum; wherein the response function is defined as the convolution product of the electromagnetic spectrum incident on the scintillation crystal, the crystal response function, the photomultiplier tube response function, and the amplifier response function. In one embodiment of the method, determining the crystal response function includes generating an impulse response matrix for the scintillation crystal through Monte Carlo simulations based on characteristics of: the scintillation crystal, a source of the electromagnetic radiation actually received by the scintillation crystal, and the geometric arrangement of the source and the scintillation crystal with respect to one another. Further, the method can also include storing the modeled response function of the detector assembly in a memory device of a control unit of a multiphase flow meter to enable the control unit to subsequently determine count rates of discrete energy levels of electromagnetic radiation actually received by the scintillation crystal of the detector assembly based on the modeled response function and on comparison of a measured spectrum resulting from the electromagnetic radiation actually received by the scintillation crystal to the modeled response function.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A method comprising:
transmitting electromagnetic radiation through a fluid, the electromagnetic radiation including x-ray or gamma radiation;
receiving a portion of the electromagnetic radiation at a detector; and
analyzing the fluid based on the portion of the electromagnetic radiation received at the detector, wherein analyzing the fluid includes:
measuring the energy spectrum of the portion of the electromagnetic radiation received by the detector;
using, via a processor, the measured energy spectrum and a physical model of detector response to electromagnetic radiation to infer incident count rates for discrete energy levels of the portion of the electromagnetic radiation received by the detector, wherein:
the physical model includes a detector response function that is based on physical characteristics of the detector and on a component response function for each of multiple components of a detection chain for the detector that relates inputs at each of the multiple components to corresponding outputs; the multiple components of the detection chain include a first component and a second component that receives an output from the first component; and the component response function for each of the multiple components of the detection chain includes a first component response function that relates an input at the first component to the output from the first component and a second component response function that relates the output from the first component, as an input to the second component, to an output from the second component; and
characterizing a physical attribute of the fluid based on the inferred incident count rates.

2. The method of claim 1, wherein using the measured energy spectrum and the physical model of detector response includes comparing the measured energy spectrum to the detector response function of the physical model to infer the incident count rates.

3. The method of claim 2, wherein comparing the measured energy spectrum to the detector response function includes performing least squares optimization of the detector response function with respect to the measured energy spectrum to infer the incident count rates.

4. The method of claim 3, wherein the physical model of detector response includes energy and resolution response models having detector-specific parameters, and the method comprises inferring the detector-specific parameters from the least squares optimization between the measured energy spectrum and the detector response function.

5. The method of claim 4, comprising calibrating the detector based on the inferred detector-specific parameters.

6. The method of claim 1, wherein the fluid is a multiphase fluid and characterizing the physical attribute of the fluid includes determining phase fractions for the multiphase fluid.

7. The method of claim 4, further comprising: monitoring the health status of the detector using the measured spectrum.

8. An apparatus comprising:
a detector of electromagnetic radiation including x-rays or gamma rays the detector including a detection chain having a first component and a second component, wherein the second component is connected to receive an output from the first component as an input to the second component;
a multi-channel analyzer configured to measure an energy spectrum of electromagnetic radiation received by the detector; and
a controller configured to analyze, via a processor, a fluid through which the electromagnetic radiation is passed from an emitter to the detector, wherein such analysis includes deconvolving the measured energy spectrum using a physical model representative of the response of the detector to characterize the electromagnetic radiation received by the detector, the physical model representative of the response of the detector is based on physical characteristics of the detector and includes a component response function for each of multiple components of the detection chain for the detector, and the component response function for each of the multiple components of the detection chain includes a first component response function that relates an input at the first component to the output from the first component and a second component response function that relates the output from the first component, as the input to the second component, to an output from the second component.

9. The apparatus of claim 8, wherein the controller is configured to determine count rates for photons incident on the detector based on the deconvolution of the measured energy spectrum.

10. The apparatus of claim 8, wherein the detector is a solid-state detector.

11. The apparatus of claim 8, comprising a multiphase flow meter having the detector, the multi-channel analyzer, and the controller.

12. The apparatus of claim 11, wherein the controller is a flow computer operable to calculate phase fractions of the fluid passing through the multiphase flow meter based on the deconvolution of the measured energy spectrum using the physical model representative of the response of the detector.

13. The apparatus of claim 8, wherein the detector includes a shaping amplifier for providing to the multi-channel analyzer output pulses indicative of photons received by the detector.

14. The apparatus of claim 13, wherein the multi-channel analyzer includes a pile-up rejector configured to discard a shaping amplifier output pulse from the detector that is indicative of multiple photons received by the detector within a width of the shaping amplifier output pulse if a time interval between receipt of the multiple photons exceeds a threshold duration.

15. A method comprising:
emitting x-ray or gamma radiation into a fluid;
receiving photons of the x-ray or gamma radiation having different energies at a detector; and
analyzing, via a processor, the fluid based on the photons received at the detector, wherein analyzing the fluid includes:
measuring an energy spectrum of the photons;
using multiple monoenergetic response functions based on physical characteristics of the detector to derive spectral components of the energy spectrum for multiple energy levels of the photons;
measuring count rates for at least two energy levels of the received photons based on the derived spectral components, wherein measuring the count rates for the at least two energy levels of the received photons based on the derived spectral components includes inferring the count rates through comparing the measured energy spectrum with a physical model of detector response to electromagnetic radiation that includes response functions for multiple components of a detection chain of the detector, wherein: the multiple components of the detection chain include a first component and a second component that receives an output from the first component; the response functions for the multiple components of the detection chain include the multiple monoenergetic response functions; the multiple monoenergetic response functions relate an input at the first component to the output from the first component; and the response functions for the multiple components of the detection chain include a second component response function that relates the output from the first component, as an input to the second component, to an output from the second component; and
characterizing a physical attribute of the fluid based on the measured count rates.

16. The method of claim 15, wherein the fluid includes a multiphase fluid and receiving the photons at the detector includes receiving photons that have passed through the multiphase fluid in a conduit.

17. The method of claim 16, comprising calculating attenuation rates of the photons by the multiphase fluid for the at least two energy levels, wherein characterizing the physical attribute of the fluid includes calculating phase fractions of the multiphase fluid using the calculated attenuation rates.

18. A multiphase flow meter comprising:
a fluid conduit;
an emitter and a detector of electromagnetic radiation including x-rays or gamma rays, the emitter and the detector arranged with respect to the fluid conduit so as to enable the detector to receive photons transmitted from the emitter through a fluid within the fluid conduit, wherein the detector includes a detection chain having a scintillator, a photomultiplier tube, and an amplifier;
a multi-channel analyzer coupled to the detector to receive electrical signals from the amplifier and output a measured energy spectrum of the photons received by the detector; and
a flow computer encoded with a response model for the detector, the response model based on physical characteristics of the emitter and the detector, wherein the response model includes response functions for multiple components of the detection chain of the detector and the response functions include a response function for the scintillator, a response function for the photomultiplier tube, and a response function for the amplifier; and wherein the flow computer is operable to analyze the fluid, such analysis including comparing the measured energy spectrum with the response model to infer count rates for the photons received by the detector and characterizing a physical attribute of the fluid based on the inferred count rates.

19. The multiphase flow meter of claim 18, wherein the response model includes detector energy and resolution functions having detector-specific parameters and a set of monoenergetic response functions that model response of the scintillator to photons incident on the scintillator.

\* \* \* \* \*